(12) United States Patent
Belson et al.

(10) Patent No.: US 12,576,308 B2
(45) Date of Patent: Mar. 17, 2026

(54) FORM FEEDBACK

(71) Applicant: Tonal Systems, Inc., San Francisco, CA (US)

(72) Inventors: Brandt Belson, San Francisco, CA (US); Jeff Bendel, Walnut Creek, CA (US); Kelly Savage, Los Angeles, CA (US)

(73) Assignee: Tonal Systems, Inc., San Francisco, CA (US)

( * ) Notice: Subject to any disclaimer, the term of this patent is extended or adjusted under 35 U.S.C. 154(b) by 0 days.

(21) Appl. No.: 17/204,235

(22) Filed: Mar. 17, 2021

(65) Prior Publication Data

US 2022/0296963 A1    Sep. 22, 2022

(51) Int. Cl.
| | |
|---|---|
| *A63B 24/00* | (2006.01) |
| *A63B 71/00* | (2006.01) |
| *A63B 71/06* | (2006.01) |
| *G09B 19/00* | (2006.01) |
| *G16H 20/30* | (2018.01) |

(52) U.S. Cl.
CPC ...... *A63B 24/0062* (2013.01); *A63B 24/0075* (2013.01); *A63B 71/0054* (2013.01); *A63B 71/0622* (2013.01); *G09B 19/003* (2013.01); *G16H 20/30* (2018.01);
(Continued)

(58) Field of Classification Search
CPC ............ A63B 24/0062; A63B 24/0075; A63B 71/0054; A63B 71/0622; A63B 2024/0012; A63B 2024/0068; A63B 2071/063; A63B 2071/0655; A63B 2024/0065; A63B 2071/0625; A63B 21/0058; A63B 21/154; A63B 21/4035; A63B 24/0006; A63B 24/0087; A63B 2024/0093; A63B 2220/24; A63B 2220/40; A63B 2225/50; G16H 20/30; G16H 40/63; G16H 50/20; G16H 50/30; G16H 50/70; G09B 19/003; G09B 19/0038
See application file for complete search history.

(56) References Cited

U.S. PATENT DOCUMENTS

| | | | | |
|---|---|---|---|---|
| 11,458,364 | B2 * | 10/2022 | Ward | G06V 20/20 |
| 2010/0208945 | A1 * | 8/2010 | Te Vrugt | G09B 19/0038 |
| | | | | 382/107 |

(Continued)

FOREIGN PATENT DOCUMENTS

| | | |
|---|---|---|
| WO | 2015083067 | 6/2015 |
| WO | 2020205276 | 10/2020 |

*Primary Examiner* — Megan Anderson
*Assistant Examiner* — Jacqueline N L Loberiza
(74) *Attorney, Agent, or Firm* — Van Pelt, Yi & James LLP

(57) ABSTRACT

Detecting quality of use of an exercise machine includes detecting a path of an actuator over time during use of the exercise machine. It further includes characterize the path including generating at least one parameter associated with the path. It further includes comparing the at least one parameter associated with the detected path to a canonical parameter.
Providing feedback on quality of use of an exercise machine includes determining a quality of a use of the exercise machine. The quality of the use of the exercise machine is determined based at least in part on a detected path of an actuator over time. It further includes performing an action that is based at least in part on the determined quality of the use of the exercise machine.

15 Claims, 6 Drawing Sheets

(52) U.S. Cl.

CPC ................. *A63B 2024/0012* (2013.01); *A63B 2024/0068* (2013.01); *A63B 2071/063* (2013.01); *A63B 2071/0655* (2013.01)

(56)                    References Cited

U.S. PATENT DOCUMENTS

| 2019/0046830 | A1* | 2/2019 | Chiavegato | ........ | A63B 24/0062 |
| 2019/0099652 | A1  | 4/2019 | Orady | | |
| 2019/0209892 | A1* | 7/2019 | Miller | ............... | A63B 69/0002 |
| 2020/0047027 | A1  | 2/2020 | Ward | | |
| 2020/0047031 | A1* | 2/2020 | Orady | ............... | A63B 24/0062 |
| 2020/0261019 | A1  | 8/2020 | Sherpa | | |
| 2022/0032159 | A1  | 2/2022 | Mallard | | |
| 2023/0191200 | A1* | 6/2023 | Sands | ............... | A63B 71/0622 |
| | | | | | 482/4 |

* cited by examiner

500

Start

Determine a quality of a use of an exercise machine — 502

Perform an action based at least in part on the determined quality of the use of the exercise machine — 504

End

FORM FEEDBACK

BACKGROUND OF THE INVENTION

When performing exercises such as part of strength training, performing movements incorrectly can lead to issues such as injury. For example, a person could very easily injure themselves if they perform a deadlift and twist their back. Further, when an individual is unsure of how to perform an exercise and does not feel confident or safe when attempting to perform a movement due to the risk of injury, this may make them less likely to want to work out. Even if an individual does not injure themselves, performing movements incorrectly can reduce the efficacy of performing the exercise, such that the user does not derive the benefits of performing the exercise.

BRIEF DESCRIPTION OF THE DRAWINGS

Various embodiments of the invention are disclosed in the following detailed description and the accompanying drawings.

DETAILED DESCRIPTION

Figure 1A:
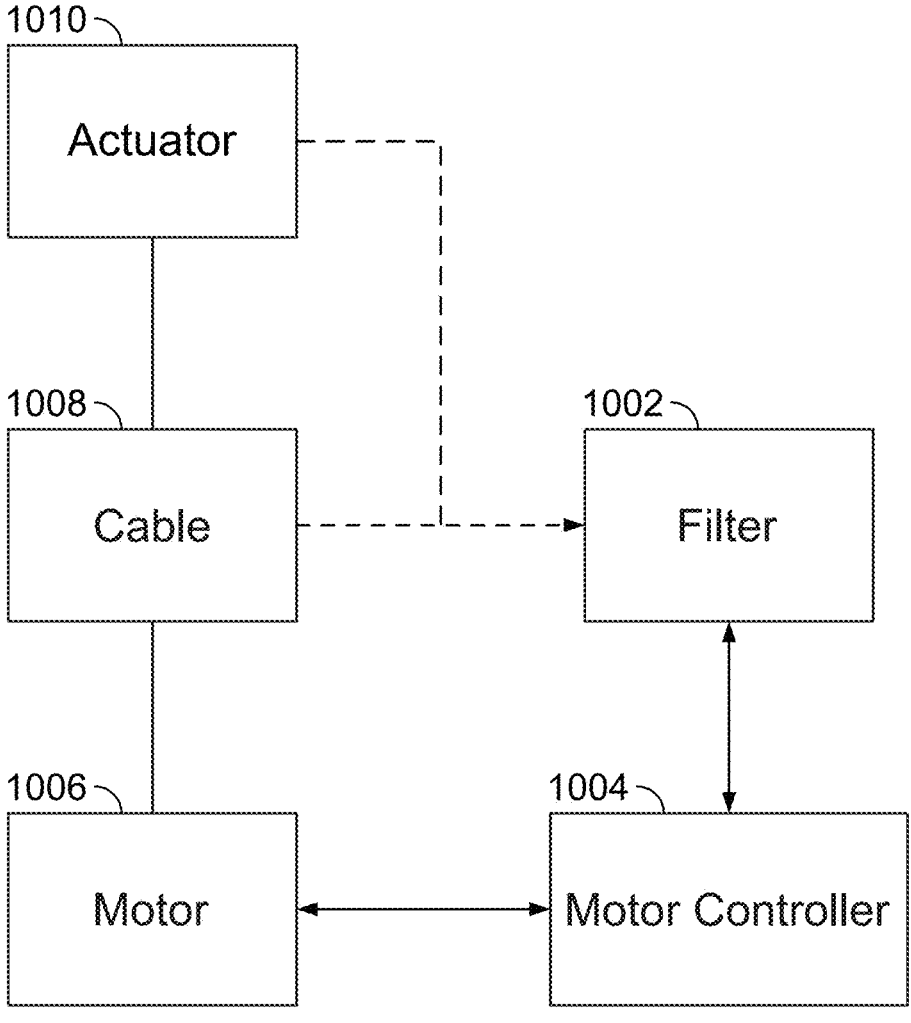
FIG. 1A illustrates an embodiment of an exercise machine.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Described herein are techniques for determining and providing training guidance and form feedback. The training guidance and form feedback techniques described herein have various benefits, such as helping users to avoid injury when performing exercises, increasing their confidence to work out and lift heavy weights (e.g., by lowering the risk of performing a movement incorrectly and allowing users to feel safe when performing exercises), and increasing the effectiveness of performing movements. Without the automated form feedback techniques described herein, users would need to receive such guidance from trained professionals such as personal trainers, who can be expensive, subjective, and who are unable to record detailed histories and data about the user's performance and progress over time.

As will be described in further detail below, using the techniques described herein, feedback is provided in the event that an exercise is being done incorrectly. The user's training (e.g., strength training) may be enhanced by providing guidance based on the detected form. The guidance may be provided in various ways, including long-term workout/exercise selection to assist achieving fitness goals, and mid-term workout/exercise selection to maximize the efficacy out of an upcoming workout, as well as during workouts in real-time to keep a user's form correct for improved efficacy and to prevent injury. As will be described in further detail below, in some embodiments, the training guidance is facilitated by providing instructions to alter their form (e.g., by providing personalized insertion of instructions). The feedback on form (also referred to herein as "form feedback") may be provided in real-time. Personalized training guidance may be inserted at various points, such as in a future next workout, a next workout, in the next month, etc.

Existing techniques for determining form include using cameras. However, existing camera-based techniques for form detection are inaccurate. For example, existing techniques for pose estimation are based on computer vision. Within computer vision, existing techniques include marker-less and marker-based. Marker-based systems include the use of markers that are placed on a user's body that track how the user moves. However, existing solutions that use such trackers may be inconvenient. While existing markerless systems may be easier to use, they are also less accurate.

The techniques described herein provide more accurate and effective form detection compared with existing techniques for evaluating form.

For illustrative purposes, embodiments of form detection, training guidance, and form feedback when performing exercises or movements using digital strength training machines are described. The training guidance, form detection, and form feedback techniques described herein may be variously adapted to accommodate any other type of exercise machine, as appropriate.

In some embodiments, detecting form and providing form feedback includes determining a quality of a use of an exercise machine (e.g., weight training machine). The quality of the use of the exercise machine is determined based at least in part on measurements associated with an actuator over time. An action is performed that is based at least in part on the determined quality of the use of the exercise machine.

In some embodiments, detecting quality of a use of an exercise machine includes detecting a spatio-temporal path of an actuator (and sensor) over time. It further includes characterizing the path including generating at least one parameter associated with the path. It further includes comparing the parameter to a canonical parameter associated with a similar path.

Example Digital Strength Trainer

FIG. 1A illustrates an embodiment of an exercise machine. In particular, the exercise machine of FIG. 1A is an example of a digital strength training machine. In some embodiments, a digital strength trainer uses electricity to generate tension/resistance. Examples of electronic resistance include using an electromagnetic field to generate tension/resistance, using an electronic motor to generate tension/resistance, and using a three-phase brushless direct-current (BLDC) motor to generate tension/resistance. In various embodiments, the form detection and feedback techniques described herein may be variously adapted to accommodate other types of exercise machines using different types of load elements without limitation, such as exercise machines based on pneumatic cylinders, springs, weights, flexing nylon rods, elastics, pneumatics, hydraulics, and/or friction.

Such a digital strength trainer using electricity to generate tension/resistance is also versatile by way of using dynamic resistance, such that tension/resistance may be changed nearly instantaneously. When tension is coupled to position of a user against their range of motion, the digital strength trainer may apply arbitrary applied tension curves, both in terms of position and in terms of phase of the movement: concentric, eccentric, and/or isometric. Furthermore, the shape of these curves may be changed continuously and/or in response to events; the tension may be controlled continuously as a function of a number of internal and external variables including position and phase, and the resulting applied tension curve may be pre-determined and/or adjusted continuously in real time.

The example exercise machine of FIG. 1A includes the following:

a motor controller circuit (1004), which in some embodiments includes a processor, inverter, pulse-width-modulator, and/or a Variable Frequency Drive (VFD);

a motor (1006), for example, a three-phase brushless DC driven by the controller circuit (1004). While a single motor is shown in this example, other numbers of motors may be used. For example, dual motors may be used;

a spool/hub with a cable (1008) wrapped around the spool and coupled to the spool. On the other end of the cable an actuator (1010) is coupled in order for a user to grip and pull on. Examples of actuators include handles and bars that are attached to the cables. The actuators may be attached to the cables at distal ends of the arms of the exercise machine, which are described in further detail below. The spool is coupled to the motor (1006) either directly or via a shaft/belt/chain/gear mechanism;

a filter (1002), to digitally control the controller circuit (1004) based on receiving information from the cable (1008) and/or actuator (1010);

optionally (not shown in FIG. 1A) a gearbox between the motor and spool. Gearboxes multiply torque and/or friction, divide speed, and/or split power to multiple spools. A number of combinations of motor and gearbox may also be used. A cable-pulley system may be used in place of a gearbox, and/or a dual motor may be used in place of a gearbox;

one or more of the following sensors (not shown in FIG. 1A):

encoders: In various embodiments, encoders are used to measure cable lengths (e.g., left and right cable lengths in this example), cable speeds, weight (tension), etc.

One example of an encoder is a position encoder; a sensor to measure position of the actuator (1010) or motor (1006). Examples of position encoders include a hall effect shaft encoder, grey-code encoder on the motor/spool/cable (1008), an accelerometer in the actuator/handle (1010), optical sensors, position measurement sensors/methods built directly into the motor (1006), and/or optical encoders. In one embodiment, an optical encoder is used with an encoding pattern that uses phase to determine direction associated with the low resolution encoder. Other mechanisms that measure back-EMF (back electromagnetic force) from the motor (1006) in order to calculate position may also be used;

a motor power sensor; a sensor to measure voltage and/or current being consumed by the motor (1006);

a user tension sensor; a torque/tension/strain sensor and/or gauge to measure how much tension/force is being applied to the actuator (1010) by the user. In one embodiment, a tension sensor is built into the cable (1008). Alternatively, a strain gauge is built into the motor mount holding the motor (1006). As the user pulls on the actuator (1010), this translates into strain on the motor mount which is measured using a strain gauge in a Wheatstone bridge configuration. In another embodiment, the cable (1008) is guided through a pulley coupled to a load cell. In another embodiment, a belt coupling the motor (1006) and cable spool or gearbox (1008) is guided through a pulley coupled to a load cell. In another embodiment, the resistance generated by the motor (1006) is characterized based on the voltage, current, or frequency input to the motor.

Another example of sensors includes inertial measurement units (IMUs). In some embodiments, IMUs are used to measure the acceleration and rate of rotation of actuators. The IMUs may be embedded within or attached to actuators (e.g., in both handles or as an attachment on a bar).

In some embodiments, an IMU is placed on the cable (e.g., via a clip) to determine inertial measurements with respect to the cable. As another example, IMUs may be included in a device that clips onto an actuator accessory such as a bar handle.

Another example type of sensor used by the exercise machine includes cameras.

In some embodiments, the exercise machine includes an embedded camera.

In some embodiments, the exercise machine is communicatively coupled (either in a wired or wireless manner) with a dedicated accessory camera external to the exercise machine that is paired with the exercise machine. The dedicated accessory camera may be set up in a different location to the exercise machine, such as on an adjacent wall, above the exercise machine on the same wall, on a tripod, etc.

In some embodiments, the exercise machine is paired with an external device that has or is attached to a camera, where such devices include mobile phones, tablets, computers, etc.

Various types of cameras may be used. As one example, RGB cameras are used. As another example, cameras with depth-sensing capability are used.

In some embodiments, infrared cameras are used that measure heat, where in some embodiments such information is used to deduce quantities such as muscle exertion, soreness, etc.

In some embodiments, the sensors used by the exercise machine include accessories such as smart watches, with which the exercise machine may be communicatively coupled (e.g., via a wireless connection such as Bluetooth or WiFi). The readings from such sensors may then be used to monitor form.

Other examples of accessories that may be communicatively coupled with the exercise machine include: smart clothing that measures muscle engagement or movement; and smart mats or smart benches that measure spatial distribution of force when the user is on them.

In some embodiments, the exercise machine includes mechanisms to locate devices (e.g., actuators, IMUs, etc.) in 3-Dimensional space. As one example, Bluetooth Low Energy (BLE) spatial locationing (e.g., Angle of Arrival and Angle of Departure "AoA/AoD") is used to locate devices in 3-D space.

In one embodiment, a three-phase brushless DC motor (1006) is used with the following:

a controller circuit (1004) combined with the filter (1002) that includes:

a processor that runs software instructions;

three pulse width modulators (PWMs), each with two channels, modulated at 20 kHz;

six transistors in an H-Bridge configuration coupled to the three PWMs;

optionally, two or three ADCs (Analog to Digital Converters) monitoring current on the H-Bridge; and/or optionally, two or three ADCs monitoring back-EMF voltage;

the three-phase brushless DC motor (1006), which in some embodiments includes a synchronous-type and/or asynchronous-type permanent magnet motor, such that:

the motor (1006) may be in an "out-runner configuration" as described below;

the motor (1006) may have a maximum torque output of at least 60 Nm and a maximum speed of at least 300 RPMs;

optionally, with an encoder or other method to measure motor position;

a cable (1008) wrapped around the body of the motor (1006) such that the entire motor (1006) rotates, so the body of the motor is being used as a cable spool in one embodiment. Thus, the motor (1006) is directly coupled to a cable (1008) spool. In one embodiment, the motor (1006) is coupled to a cable spool via a shaft, gearbox, belt, and/or chain, allowing the diameter of the motor (1006) and the diameter of the spool to be independent, as well as introducing a stage to add a set-up or step-down ratio if desired. Alternatively, the motor (1006) is coupled to two spools with an apparatus in between to split or share the power between those two spools. Such an apparatus could include a differential gearbox, or a pulley configuration; In some embodiments, the two motors (dual motor configuration) are each coupled with a respective spool.

an actuator (1010) such as a handle, a bar, a strap, or other accessory connected directly, indirectly, or via a connector such as a carabiner to the cable (1008).

In some embodiments, the controller circuit (1002, 1004) is programmed to drive the motor in a direction such that it draws the cable (1008) towards the motor (1006). The user pulls on the actuator (1010) coupled to the cable (1008) against the direction of pull of the motor (1006).

One example purpose of this setup is to provide an experience to a user similar to using a traditional cable-based strength training machine, where the cable is attached to a weight stack being acted on by gravity. Rather than the user resisting the pull of gravity, they are instead resisting the pull of the motor (1006).

Note that with a traditional cable-based strength training machine, a weight stack may be moving in two directions: away from the ground or towards the ground. When a user pulls with sufficient tension, the weight stack rises, and as that user reduces tension, gravity overpowers the user and the weight stack returns to the ground.

By contrast in a digital strength trainer, there is no actual weight stack. The notion of the weight stack is one modeled by the system. The physical embodiment is an actuator (1010) coupled to a cable (1008) coupled to a motor (1006). A "weight moving" is instead translated into a motor rotating. As the circumference of the spool is known and how fast it is rotating is known, the linear motion of the cable may be calculated to provide an equivalency to the linear motion of a weight stack. Each rotation of the spool equals a linear motion of one circumference or $2\pi r$ for radius r. Likewise, torque of the motor (1006) may be converted into linear force by multiplying it by radius r.

If the virtual/perceived "weight stack" is moving away from the ground, motor (1006) rotates in one direction. If the "weight stack" is moving towards the ground, motor (1006) rotates in the opposite direction. Note that the motor (1006) is pulling towards the cable (1008) onto the spool. If the cable (1008) is unspooling, it is because a user has overpowered the motor (1006). Thus, note a distinction between the direction the motor (1006) is pulling, and the direction the motor (1006) is actually turning.

If the controller circuit (1002, 1004) is set to drive the motor (1006) with, for example, a constant torque in the direction that spools the cable, corresponding to the same direction as a weight stack being pulled towards the ground, then this translates to a specific force/tension on the cable (1008) and actuator (1010). Referring to this force as "Target Tension," in one embodiment, this force is calculated as a function of torque multiplied by the radius of the spool that the cable (1008) is wrapped around, accounting for any additional stages such as gear boxes or belts that may affect the relationship between cable tension and torque. If a user pulls on the actuator (1010) with more force than the Target Tension, then that user overcomes the motor (1006) and the cable (1008) unspools moving towards that user, being the virtual equivalent of the weight stack rising. However, if that user applies less tension than the Target Tension, then the motor (1006) overcomes the user and the cable (1008) spools onto and moves towards the motor (1006), being the virtual equivalent of the weight stack returning.

BLDC Motor. While many motors exist that run in thousands of revolutions per second, an application such as fitness equipment designed for strength training has different requirements and is by comparison a low speed, high torque type application suitable for certain kinds of BLDC motors configured for lower speed and higher torque.

In one embodiment, a specification of such a motor (1006) is that a cable (1008) wrapped around a spool of a given diameter, directly coupled to a motor (1006), behaves like a 200 lbs weight stack, with the user pulling the cable at a maximum linear speed of 62 inches per second. The aforementioned weight and linear speed specifications are but examples for illustrative purposes, and the system may be configured to behave to different specifications. A number of motor parameters may be calculated based on the diameter of the spool.

TABLE 1

| User Requirements | | | | | |
|---|---|---|---|---|---|
| Target Weight | 200 lbs | | | | |
| Target Speed | 62 inches/sec = 1.5748 meters/sec | | | | |

| Requirements by Spool Size | | | | | |
|---|---|---|---|---|---|
| Diameter (inches) | | | | | |
| 3 | 5 | 6 | 7 | 8 | 9 |
| RPM 394.7159 | 236.82954 | 197.35795 | 169.1639572 | 148.0184625 | 131.5719667 |
| Torque (Nm) 67.79 | 112.9833333 | 135.58 | 158.1766667 | 180.7733333 | 203.37 |
| Circumference (inches) 9.4245 | 15.7075 | 18.849 | 21.9905 | 25.132 | 28.2735 |

Thus, a motor with 67.79 Nm of force and a top speed of 395 RPM, coupled to a spool with a 3 inch diameter meets these requirements.

Hub motors are three-phase permanent magnet BLDC direct drive motors in an "out-runner" configuration: throughout this specification, the "out-runner" configuration refers to the permanent magnets being placed outside the stator rather than inside, as opposed to many motors which have a permanent magnet rotor placed on the inside of the stator as they are designed more for speed than for torque. Out-runners have the magnets on the outside, allowing for a larger magnet and pole count and are designed for torque over speed. Another way to describe an out-runner configuration is when the shaft is fixed and the body of the motor rotates.

Hub motors also tend to be "pancake style." As described herein, pancake motors are higher in diameter and lower in depth than most motors. Pancake style motors are advantageous for a wall mount, subfloor mount, and/or floor mount application where maintaining a low depth is desirable, such as a piece of fitness equipment to be mounted in a consumer's home or in an exercise facility/area. As described herein, a pancake motor is a motor that has a diameter higher than twice its depth. As one example, a pancake motor is between 15 and 60 centimeters in diameter, for example, 22 centimeters in diameter, with a depth between 6 and 15 centimeters, for example, a depth of 6.7 centimeters.

Motors may also be "direct drive," meaning that the motor does not incorporate or require a gear box stage. Many motors are inherently high speed low torque but incorporate an internal gearbox to gear down the motor to a lower speed with higher torque and may be called gear motors. Direct drive motors may be explicitly called as such to indicate that they are not gear motors.

If a motor does not exactly meet the requirements illustrated in the table above, the ratio between speed and torque may be adjusted by using gears or belts to adjust. A motor coupled to a 9" sprocket, coupled via a belt to a spool coupled to a 4.5" sprocket doubles the speed and halves the torque of the motor. Alternately, a 2:1 gear ratio may be used to accomplish the same thing. Likewise, the diameter of the spool may be adjusted to accomplish the same.

Alternately, a motor with 100× the speed and 100th the torque may also be used with a 100:1 gearbox. As such a gearbox also multiplies the friction and/or motor inertia by 100×, torque control schemes become challenging to design for fitness equipment/strength training applications. Friction may then dominate what a user experiences. In other applications friction may be present, but is low enough that it is compensated for, but when it becomes dominant, it is difficult to control for. For these reasons, direct control of motor torque is more appropriate for fitness equipment/strength training systems. This would typically lead to the selection of an induction type motor for which direct control of torque is simple. Although BLDC motors are more directly able to control speed and/or motor position rather than torque, torque control of BLDC motors can be made possible when used in combination with an appropriate encoder.

Figure 1B:
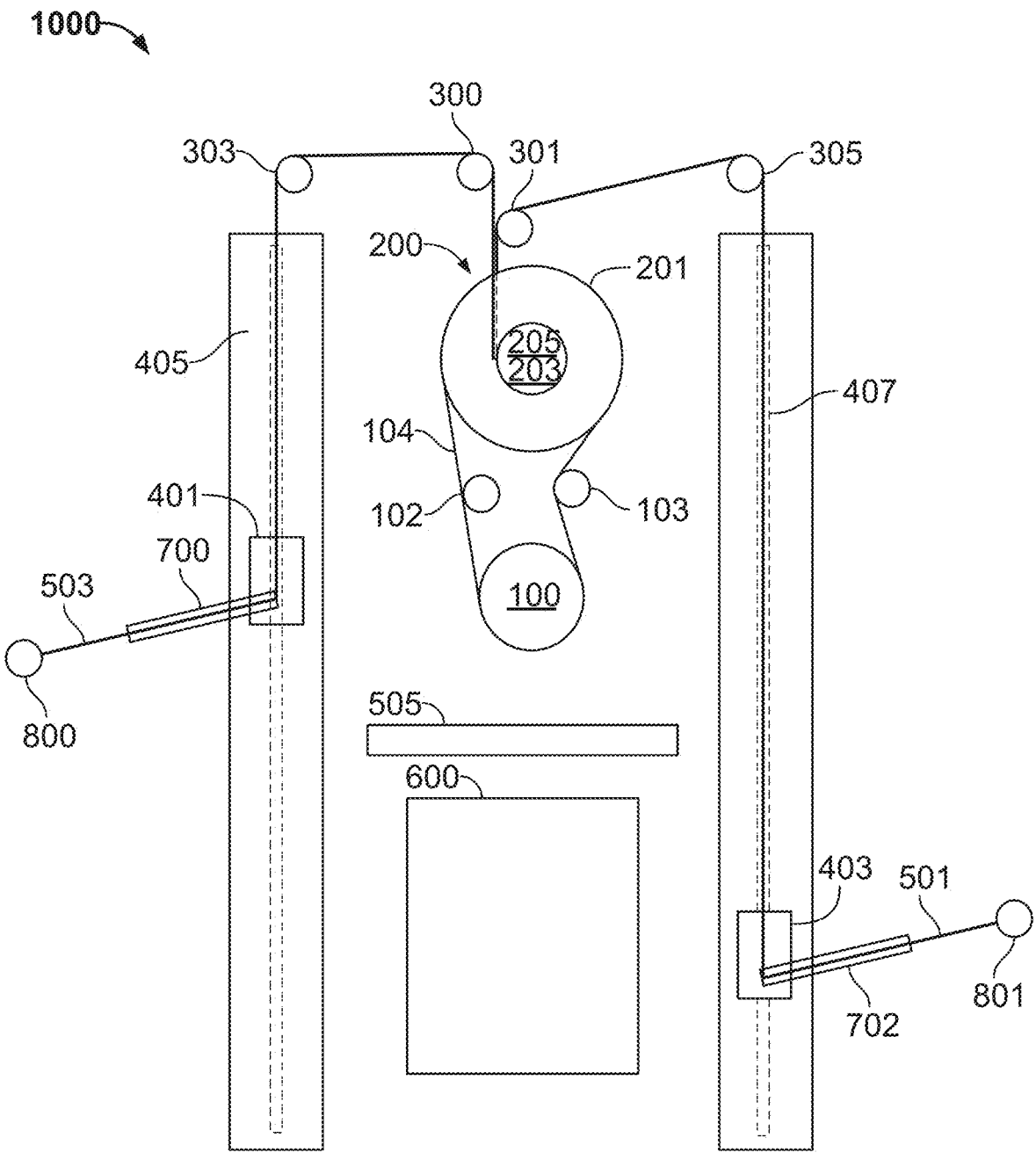
FIG. 1B illustrates a front view of one embodiment of an exercise machine.

FIG. 1B illustrates a front view of one embodiment of an exercise machine. In some embodiments, exercise machine 1000 of FIG. 1B is an example or alternate view of the exercise machine of FIG. 1A. In this example, exercise machine (1000) includes a pancake motor (100), a torque controller coupled to the pancake motor, and a high resolution encoder coupled to the pancake motor (102). As used herein, a "high resolution" encoder refers to an encoder with 30 degrees or greater of electrical angle. In this example, two cables (503) and (501) are coupled respectively to actuators (800) and (801) on one end of the cables. The two cables (503) and (501) are coupled directly or indirectly on the opposite end to the motor (100). While an induction motor may be used for motor (100), a BLDC motor may also be used for its cost, size, weight, and performance. In some embodiments, a high resolution encoder assists the system to determine the position of the BLDC motor to control torque. While an example involving a single motor is shown, the exercise machine may include other configurations of motors, such as dual motors, with each cable coupled to a respective motor.

Sliders (401) and (403) may be respectively used to guide the cable (503) and (501) respectively along rails (405) and (407). The exercise machine in FIG. 1B translates motor torque into cable tension. As a user pulls on actuators (800) and/or (801), the machine creates/maintains tension on cable (503) and/or (501). The actuators (800, 801) and/or cables (503, 501) may be actuated in tandem or independently of one another.

In one embodiment, electronics bay (600) is included and has the necessary electronics to drive the system. In one embodiment, fan tray (505) is included and has fans that cool the electronics bay (600) and/or motor (100).

Motor (100) is coupled by belt (104) to an encoder (102), an optional belt tensioner (103), and a spool assembly (200). In one embodiment, motor (100) is an out-runner, such that the shaft is fixed and the motor body rotates around that shaft. In one embodiment, motor (100) generates torque in the counter-clockwise direction facing the machine, as in the example in FIG. 1B. Motor (100) has teeth compatible with the belt integrated into the body of the motor along the outer circumference. Referencing an orientation viewing the front of the system, the left side of the belt (104) is under tension, while the right side of the belt is slack. The belt tensioner (103) takes up any slack in the belt. An optical rotary encoder (102) coupled to the tensioned side of the belt (104) captures all motor movement, with significant accuracy because of the belt tension. In one embodiment, the optical rotary encoder (102) is a high resolution encoder. In one embodiment, a toothed belt (104) is used to reduce belt slip. The spools rotate counter-clockwise as they are spooling cable/taking cable in, and clockwise as they are unspooling/releasing cable out.

Spool assembly (200) comprises a front spool (203), rear spool (205), and belt sprocket (201). The spool assembly (200) couples the belt (104) to the belt sprocket (201), and couples the two cables (503) and (501) respectively with spools (205) and (203). Each of these components is part of a low profile design. In one embodiment, a dual motor configuration not shown in FIG. 1B is used to drive each cable (503) and (501). In the example shown in FIG. 1B, a single motor (100) is used as a single source of tension, with a plurality of gears configured as a differential are used to allow the two cables/actuators to be operated independently or in tandem. In one embodiment, spools (205) and (203) are directly adjacent to sprocket (201), thereby minimizing the profile of the machine in FIG. 1B.

As shown in FIG. 1B, two arms (700, 702), two cables (503, 501) and two spools (205, 203) are useful for users with two hands, and the principles disclosed without limitation may be extended to three, four, or more arms (700) for quadrupeds and/or group exercise. In one embodiment, the plurality of cables (503, 501) and spools (205, 203) are driven by one sprocket (201), one belt (104), and one motor (100), and so the machine (1000) combines the pairs of devices associated with each user hand into a single device. In other embodiments, each arm is associated with its own motor and spool.

In one embodiment, motor (100) provides constant tension on cables (503) and (501) despite the fact that each of cables (503) and (501) may move at different speeds. For example, some physical exercises may require use of only one cable at a time. For another example, a user may be stronger on one side of their body than another side, causing differential speed of movement between cables (503) and (501). In one embodiment, a device combining dual cables (503) and (501) for a single belt (104) and sprocket (201) retains a low profile, in order to maintain the compact nature of the machine, which can be mounted on a wall.

In one embodiment, pancake style motor(s) (100), sprocket(s) (201), and spools (205, 203) are manufactured and arranged in such a way that they physically fit together within the same space, thereby maximizing functionality while maintaining a low profile.

As shown in FIG. 1B, spools (205) and (203) are respectively coupled to cables (503) and (501) that are wrapped around the spools. The cables (503) and (501) route through the system to actuators (800) and (801), respectively.

The cables (503) and (501) are respectively positioned in part by the use of "arms" (700) and (702). The arms (700) and (702) provide a framework for which pulleys and/or pivot points may be positioned. The base of arm (700) is at arm slider (401) and the base of arm (702) is at arm slider (403).

The cable (503) for a left arm (700) is attached at one end to actuator (800). The cable routes via arm slider (401) where it engages a pulley as it changes direction, then routes along the axis of rotation of track (405). At the top of rail/track (405), fixed to the frame rather than the track, is pulley (303) that orients the cable in the direction of pulley (300), that further orients the cable (503) in the direction of spool (205), wherein the cable (503) is wound around spool (205) and attached to spool (205) at the other end.

Similarly, the cable (501) for a right arm (702) is attached at one end to actuator (801). The cable (501) routes via slider (403) where it engages a pulley as it changes direction, then routes along the axis of rotation of rail/track (407). At the top of the rail/track (407), fixed to the frame rather than the track is pulley (305) that orients the cable in the direction of pulley (301), that further orients the cable in the direction of spool (203), wherein the cable (501) is wound around spool (203) and attached to spool (203) at the other end.

One use of pulleys (300, 301) is that they permit the respective cables (503, 501) to engage respective spools (205, 203) "straight on" rather than at an angle, wherein "straight on" references being within the plane perpendicular to the axis of rotation of the given spool. If the given cable were engaged at an angle, that cable may bunch up on one side of the given spool rather than being distributed evenly along the given spool.

In the example shown in FIG. 1B, pulley (301) is lower than pulley (300). This demonstrates the flexibility of routing cables. In one embodiment, mounting pulley (301) leaves clearance for certain design aesthetic elements that make the machine appear to be thinner.

In one embodiment, the exercise machine/appliance passes a load/resistance against the user via one or more lines/cables, to a grip(s) (examples of an actuator) that a user displaces to exercise. A grip may be positioned relative to the user using a load arm and the load path to the user may be steered using pulleys at the load arm ends, as described above. The load arm may be connected to a frame of the exercise machine using a carriage that moves within a track that may be affixed to the main part of the frame. In one embodiment, the frame is firmly attached to a rigid structure such as a wall. In some embodiments, the frame is not mounted directly to the wall. Instead, a wall bracket is first mounted to the wall, and the frame is attached to the wall bracket. In other embodiments, the exercise machine is mounted to the floor. The exercise machine may be mounted to both the floor and the wall for increased stability. In other embodiments, the exercise machine is a freestanding device.

In some embodiments, the exercise machine includes a media controller and/or processor, which monitors/measures user performance (for example, using the one or more sensors described above), and determines loads to be applied to the user's efforts in the resistance unit (e.g., motor described above). Without limitation, the media controller and processor may be separate control units or combined in a single package. In some embodiments, the controller is further coupled to a display/acoustic channel that allows instructional information to be presented to a user and with which the user interacts in a visual manner, which includes communication based on the eye such as video and/or text or icons, and/or an auditory manner, which includes communication based on the ear such as verbal speech, text-to-speech synthesis, and/or music. Collocated with an information channel is a data channel that passes control program information to the processor which generates, for example, exercise loading schedules. In some embodiments, the display is embedded or incorporated into the exercise machine, but need not be (e.g., the display or screen may be separate from the exercise machine, and may be part of a separate device such as a smartphone, tablet, laptop, etc. that may be communicatively coupled (e.g., either in a wired or wireless manner) to the exercise machine). In one embodiment, the display is a large format, surround screen representing a virtual reality/alternate reality environment to the user; a virtual reality and/or alternate reality presentation may also be made using a headset.

In one embodiment, the appliance media controller provides audio information that is related to the visual information from a program store/repository that may be coupled to external devices or transducers to provide the user with an auditory experience that matches the visual experience. Control instructions that set the operational parameters of the resistance unit for controlling the load or resistance for the user may be embedded with the user information so that the media package includes information usable by the controller to run the machine. In this way a user may choose an exercise regime and may be provided with cues, visual and auditory as appropriate, that allow, for example, the actions of a personal trainer to be emulated. The controller may further emulate the actions of a trainer using an expert system and thus exhibit artificial intelligence. The user may better form a relationship with the emulated coach or trainer, and this relationship may be encouraged by using emotional/mood cues whose effect may be quantified based on performance metrics gleaned from exercise records that track user performance in a feedback loop using, for example, the sensor(s) described above.

Figure 2:
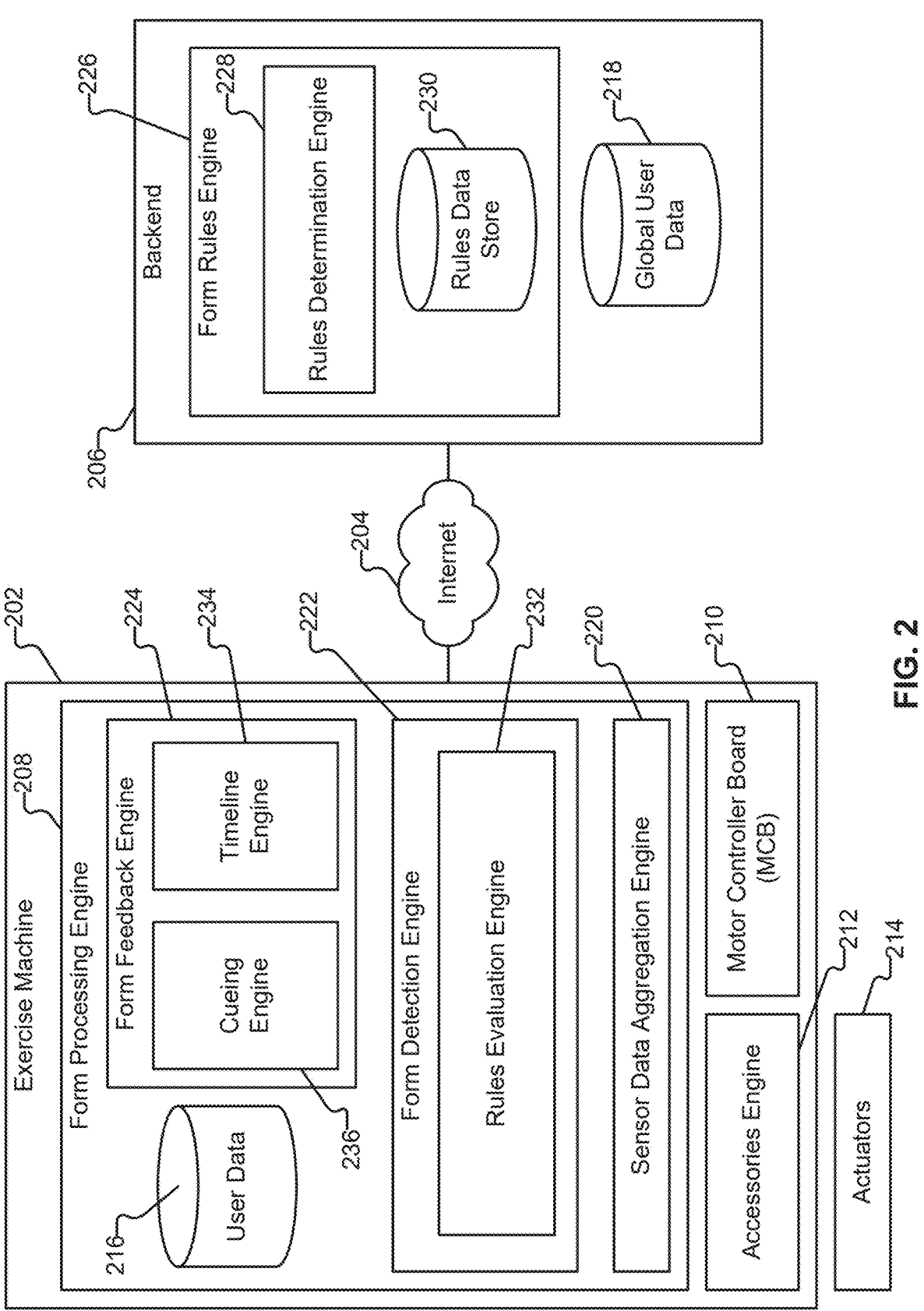
FIG. 2 illustrates an embodiment of a system for detecting form and providing form feedback.

FIG. 2 illustrates an embodiment of a system for detecting form and providing form feedback. In this example, exercise machine 202 is an alternate view of the exercise machine embodiments shown in FIGS. 1A and 1B. As shown in this example, exercise machine 202 also communicates (over a network 204 such as the Internet) with backend 206. For illustrative purposes, examples involving a digital strength trainer with two arms are described.

In this example, exercise machine 202 includes form processing engine 208, motor controller board 210 (an example of motor controller 1004), accessories engine 212, and actuators 214. In some embodiments, these elements are compute/sensor nodes that form a computation architecture/stack in which sensor measurements are taken, and computations on such sensor measurements are made, at various levels.

In this example, at the bottom level/layer of the stack are actuators/accessories 214, examples of which include handles, bar controllers, smart mats, etc. In some embodiments, the sensors at the level of actuators 214 include IMUs, buttons, force sensors, etc.

At the next level of the computation architecture is accessories engine 212. Accessories engine 212 is configured to aggregate sensor data from the actuators. As one example, accessories engine 212 is implemented using the BLE (Bluetooth Low Energy) Central plugin, which communicates with accessories (e.g., via BLE, USB, RF, etc.). In some embodiments, the accessories engine is configured to determine the positions of accessories/actuators in physical space.

At the next level of the computation stack is motor controller board (MCB) 210. MCB 210 is another example of a computation node/layer in the computation architecture. In this example, the motor controller board collects data such as cable position and speed, motor position and speed, cable tension, scalable stack information (e.g., health of the motor, board, processor/memory of the board, and communication), etc. As one example, the motor controller board (MCB) is configured to receive encoder messages and determine right and left cable lengths. For example, the motor controller board is configured to receive encoder messages and determine right and left cable lengths. In some embodiments, the MCB provides such sensor readings to form processing engine 202. The information may be sent via a communication bus such as a USB (Universal Serial Bus). The information may be sent periodically (e.g., at a frequency of 50 Hz).

In the next layer of the computation architecture is form processing engine 208. In some embodiments, form processing engine 208 is a portion of an exercise application running on a computing device included or otherwise associated with the exercise machine. As one example, the application is an Android application running on a computing device such as an Android tablet or computing device embedded in the exercise machine. In this example, form processing engine 208 is configured to monitor form, detect instances of bad or incorrect form, and provide form feedback by processing sensor data (e.g., from accessories and the MCB), as well as user data stored in user data store 216 (e.g., user profile, measurements, goals, suggested weights, etc.), workout data (e.g., current move, aggregate muscle utilization, movement attributes such as one or two-sided, etc.), camera and microphone information, etc.

As will be described in further detail below, monitoring form includes computing various variables. For example, the form processing engine detects repetitions as well as phases of a repetition. The form processing engine also computes aggregate metrics for each phase of a repetition, such as distance in the eccentric phase, the average speed in the concentric phase, etc. The computation of the variables is used to determine the path of the actuators in physical space over time.

To detect bad or incorrect form, the form processing engine then evaluates the computed variables as inputs to another layer of processing, which in various embodiments includes signal processing, machine learning, statistics, etc. The output variables from these algorithms/layer of processing are compared against a set of rules. (In other embodiments, the rules may also be used to detect good form). In some embodiments, the rules are used to evaluate the determined or detected actuator path to determine if the path (in 3D space and over time) is indicative of bad form.

In some embodiments, a rule defines a set of conditions that are checked for. If the conditions are met, then bad form is detected. The conditions include measurement conditions, where sensor measurements that are obtained are evaluated against the conditions defining bad form. Each movement or exercise has a corresponding set of conditions or rules usable to detect bad form with respect to the exercise.

In some embodiments, each rule further defines a type of form feedback to provide in response to detection of a form event. For example, each rule further has a specific set of cues such as voiceover or text that are actions to be taken in response to triggering of the rule. In some embodiments, a form detection rule includes an expression that compares calculated parameters that characterize the path of the actuator (calculated using the sensor measurements taken during performance of the exercise movement) against canonical parameters. The rule is triggered when the result of evaluation of the expression indicates that incorrect form has been detected. Various types of form feedback and training guidance may then be provided in response to the detection of the instance of incorrect form. Further examples and details regarding rules, form feedback, and training guidance are provided below.

In some embodiments, the form detection rules are received from backend 206. As one example, a rule is written as a string that contains a set of variables. The application on the exercise machine is configured to download the rules from the server and evaluate the rules (e.g., using rules evaluation engine 232). In this case, the application need not know the rules. This infrastructure provides flexibility in that changes to rules or the addition of more rules is performed on the server (backend 206), without having to release a new version of the application to client exercise machines.

In some embodiments, backend 206 provides to exercise machine 202 rules as text that is parsed and used by the client exercise machine 202. This implementation also works well even in the presence of intermittent WiFi. As another example, the client exercise machine 202 sends data (e.g., sensor measurement data) to the backend 206 (e.g., via persistent websockets with low latency), and backend 206 evaluates if a trigger should fire or not (e.g., the form event detection is performed remotely, rather than locally on the client, or as some combination thereof).

The next layer of the computation architecture includes backend 206. In this example, the backend compute node includes global user data store 218, which includes information aggregated from multiple users of multiple exercise machines, and includes, for example, population statistics for all or subsets of users. In one embodiments, backend 206 is implemented on Amazon EC2 instances.

As shown in this example, data and data streams, such as sensors and user information/preferences, are distributed throughout the system/computation architecture. Incorrect form may be detected at any of the distributed compute nodes in the computation architecture. Further details regarding form detection will be described below.

In some embodiments, form detection is performed based on data collected from multiple sensors. As will be described in further detail below, data may be fused, correlated, or analyzed at any compute node in a process referred to herein as "sensor fusion." The sensor data may also be passed through or pushed downwards to be operated on by various compute nodes in the computation stack.

As one example, suppose that the actuators 214 being used are two handles. The measurements taken from sensors (e.g., IMUs) in the two handles are passed to accessories engine 212 of the exercise machine, which aggregates, for example, sensor readings from all actuators. The actuator sensors data is then passed to form processing engine 208.

Sensor information collected by MCB 210 is also passed to form processing engine 208. As shown in this example, sensor data aggregation engine 220 of form processing engine 208 is configured to collect and aggregate the various and disparate sensor information (e.g., IMU sensor data, cable/motor/tension sensor data, etc.). Form detection engine 222 is then configured to detect form (e.g., incorrect form) using the combined sensor data, as well as user data.

In some embodiments, data, such as workout data (e.g., from MCB 210) and accessory data (e.g., smart bench data) is provided to backend 206.

Form feedback engine 224 of form processing engine 208 is configured to provide form feedback based on detected form events (e.g., detected instances of bad form). As will be described in further detail below, feedback may be provided in a variety of ways based on the data that is collected and the type of form that is detected. The origin of the feedback (the element from which feedback is provided) may come from any compute node in the computation architecture. For example, actuators/accessories 214 may provide feedback in the form of haptic feedback, LED feedback, etc. Feedback in the form of motor control (e.g., weight, speed, etc.) may be provided by MCB 210. Feedback such as sounds, text, content, voiceovers, cues, etc. may be provided by an application such as that running form processing engine 208. Feedback such as email, SMS, push notifications, etc., may be provided by backend 206.

In various embodiments, form detection, sensor data fusion, and feedback to the user are calculated at any of the above compute nodes in the computation architecture. In some embodiments, the algorithms and logic to perform the aforementioned form detection, sensor data fusion, and feedback calculation are distributed across the entire stack with interfaces between each to obtain optimal performance and accuracy, along with low latency. For example, tasks that require latency that is lower than is possible based on communication between layers are done at lower levels. When latency can be higher or when data is taken in aggregate (e.g., across an entire workout), then algorithms are run at higher levels where more computational power and contextual data is available.

Further details regarding form monitoring/detection and providing form feedback and training guidance are described below.

Monitoring Form

Form detection engine 222 is configured to monitor the form of the user as they perform exercise movements. In some embodiments, proper form is continuously monitored. In some embodiments, monitoring form includes detecting specific types of bad form. Various sensors are used to monitor users' form. As described above in conjunction with FIGS. 1A-1B, examples of sensors used to monitor users' form include encoders (e.g., to determine cable and/or motor position), cameras (either embedded and/or external), external accessories (e.g., smart watches, smart clothing, smart mats, smart benches), spatial sensors (e.g., BLE spatial locationing sensors), etc.

Detecting Incorrect Form

In some embodiments, each exercise or movement has a set of types of bad form which are monitored for by the exercise machine using a combination of one or more of the above sensor measurements. For example, the monitoring is performed by algorithms that use a combination of machine learning and heuristics to determine when a user is very likely to have performed bad form, based on what the user does in every repetition of the exercise. Examples of bad form detected by the form monitoring algorithms include, without limitation:

A user's range of motion has shortened over the course of a set

A user is positioned too close or too far from the exercise machine

A user's range of motion is not reaching close enough to the ground

A user's range of motion is too small or large for the move and their limb length A user's speed is too fast or too slow A user accelerated too quickly in order to "cheat" and make the first half of a repetition easier.

A user incorporates an incorrect muscle group or body part, such as using legs or lower back for a Seated Row and using legs for Bicep Curls and Lateral Raises.

A user has lost balance

A user is twisting their back

A user is moving when they should be still on an isometric hold

A user's back is not rounded, flat, or arched, depending on which is appropriate for a given movement A user's knees and hips are not bending at the right points or amounts A user's motions are asymmetric between different sides.

A user's rotating their wrists when they should not or vice versa.

A user's spatial path of motion is not correct, such as not vertical.

As shown in the examples above, incorrect form that is monitored for also takes into account performance of the movement, such as speed of the movement (e.g., too fast or too slow, as described above), force applied through the movement, etc.

As will be described in further detail below, in some embodiments, the monitoring algorithms are defined as expressions that are evaluated by performing various operations on calculated parameters (e.g., calculated using sensor measurements taken during performance of an exercise movement) that are compared with canonical parameters/values. Examples of such form detection expressions are described in further detail below.

In some embodiments, the form detection engine monitors the form of the user by determining, spatially (e.g., in 3D space) and temporally, the path of an actuator (e.g., handle, bar, or other accessory that the user is using) over time. In some embodiments, bad form is detected if the path of the actuator matches to the conditions in rules that define an incorrect quality of a movement (e.g., what is bad form for an exercise or a phase of an exercise). In some embodiments, the sensor signals are processed with algorithms including signal processing, machine learning, statistics, or other techniques to provide probabilities of types of form, correct or incorrect. In some embodiments, the conditions in the rules are defined relative to variables that are calculated from sensor measurements used to determine the path of the actuator. For example, the path of the actuator may be determined from readings from multiple sources. The readings from the different sources may be used independently or in combination. Using combinations of sensors at the same time improves accuracy of form monitoring and bad form detection. The process of combining measurements from multiple readings is referred to herein as "sensor fusion," which is described in more detail below.

As described above, in some embodiments, the parameters or conditions defining the specific types of bad form are encapsulated in expressions in form detection rules. If the conditions specified in a given rule for a specific type of bad form are met, then the rule is triggered, and a form event (e.g., instance of incorrect form) has been detected. In some embodiments, the rule also specifies an action to be taken in response to detection of the form event. Examples of actions include providing feedback and training guidance. Further details regarding rules are provided below.

The following is an example of detecting instances of incorrect form or detecting events in which incorrect form has occurred.

The example digital strength trainer described herein uses cables. One type of signal usable to monitor form and detect incorrect form is cable-related signals. Examples of cable-related signals and measurements are cable length (e.g., how much or how far a cable has been pulled out), speed of the cable, force/tension on the cable, etc. The cable-related measurements may be taken for each individual cable in the exercise machine (e.g., the two cables on the left and right side of the example exercise machine of FIG. 1B). Such cable related measurements are used to deduce or otherwise determine form or a quality of a use of the exercise machine.

For example, while a user is performing their range of motion, the encoders of the exercise machine are used to accurately determine how far the user has pulled the cable out through an entire repetition (e.g., by measuring cable length). In some embodiments, the accuracy is at a sub-inch granularity. Such accuracy may be difficult to achieve using only a camera (e.g., via computer vision techniques) or an inertial measurement unit (IMU). Thus, using the cable length detection mechanisms described herein, the exercise machine is able to, for example, detect if a user is starting to shorten their repetition because they are becoming fatigued. In this case, in response to determining that shortening of a repetition is occurring (based on evaluation of an expression that compares calculated parameters that characterize the path of the actuator using the cable measurements against canonical parameters), the exercise machine provides feedback by cueing the user to complete their repetition. Further, because of the accuracy that is achieved using the detection mechanisms described herein, asymmetries (e.g., between the pulling of the left and right cables of the exercise machine of FIG. 1B) may be detected. If the cables are supposed to have been pulled symmetrically, but they are detected to not be symmetrical, the exercise machine, in some embodiments, cues the user to the asymmetry. The exercise machine may also determine that the user is weaker on one side than the other, and provide recommendations about how they should strengthen the side that is weaker, or that they should focus on mobility, such as flexibility issues.

As described above, encoders may be used to determine cable length (e.g., the amount by which a cable has been extended from the end of an arm of the machine). Difference or delta in cable length between repetitions of a movement is also determined as described above. Absolute cable length may also be determined. The absolute cable length may be used when determining form feedback for an exercise. For example, as the circumference of the spools is known and how fast it is rotating is known (e.g., via an encoder on the motor), the linear motion of the cable may be calculated. For example, each rotation of the spool equals a linear motion of one circumference or $2\pi r$ for radius. Likewise, torque of the motor may be converted into linear force by multiplying it by radius $r$.

In some embodiments, angle of the cable is determined. As one example, the length of the cable, in conjunction with the position of an arm, may be used to determine that the cable is within a range of angles. The estimate of the angle of the cable may also be used as an input to a rule when determining whether incorrect form has been detected. For example, the cable angle may be used to deduce that a user is too close or too far from the exercise machine for the movement being performed.

In some embodiments, the arm position (e.g., the horizontal/vertical pivot angle of the arms, vertical translation height, etc.) is determined. Positioning of the arms for a movement facilitates correct form. In some embodiments, the video content that is displayed includes explanations for how to position the arms. Direct guidance may also be provided. In some embodiments, the exercise machine includes sensors in the arms that detect its orientation. Further, the exercise machine knows the correct arm setup for each move and personalizes it for the user based on knowledge about the user (e.g., demographic information such as height, weight, body mass index (BMI), sex, limb length, age, etc.). In some embodiments, the arm position is used to determine or compute the range of motion for a set.

In some embodiments, the exercise machine includes a single motor, where a differential is used to allow different cable lengths for the two arms. In this case with a single motor, two encoders may be used, where one encoder is used for determining motor position for motor control, and where the other encoder is used to determine cable position (as motor position would not translate directly to cable position). Having two types of encoders (for motor and cable position) allows left and right cable positions to be measured independently. In other embodiments, the exercise machine includes dual motors, with one motor to drive each cable. In this case, there are two encoders, one for each motor, and a separate encoder to measure cable position may not be needed.

In some embodiments, sensors are used to determine a zero position for the cables. In some embodiments, re-zeroing is performed. For example, when the cart height changes (e.g., vertical translation of the arm along sliders), sensors that are at the locked positions are used to determine whether there is a new locked position, and if there is a new locked position, then re-zeroing (i.e., recalculating of zero point) is performed. This is because as the cart height runs along a column, the amount of cable that is pulled out changes when the cart height is adjusted up or down. In some embodiments, re-zeroing is performed when the arm angle changes. In some embodiments, re-zeroing is performed if there has not been motion (e.g., the cable length/position has not changed) for a threshold amount of time. In this case, it is inferred that the actuator is against the distal end of the arm, and re-zeroing may be performed.

As one example, suppose that a user is performing a deadlift. In this example, suppose that a goal for the movement is that the user should be within three inches of the ground for the deadlift. The following is one example of how to determine whether the goal has been achieved. As described above, the absolute length of motion of the cable is determined. Sensors are used to determine where, for example, the carriage is, the vertical pivot angle of the arm, as well as the horizontal pivot angle of the arm (e.g., using sensors configured to determine the pivot angles of the arms). The position of the exercise machine relative to the floor is also known. As one example, the exercise machine is only allowed to be installed within a specification, and thus the height of the exercise machine (e.g., when wall mounted) relative to the floor is known.

In this example, during the workout, suppose that the application is receiving, periodically (e.g., at 50 Hz), encoder measurements, including right and left cable lengths, speeds, tensions, etc.

In this example, when performing the deadlift, the application detects repetitions of the deadlift movement. The repetitions are determined based on cable length signals. In some embodiments, the repetitions are determined based on identifying maximums and minimums in the cable length signals. Checks are also performed to filter out spurious signals that are not actually repetitions. In one embodiment, the application determines what phase of a repetition (and what part of the phase, such as beginning or end) the user is in. Different types of bad or poor form are monitored for based on what phase of the repetition (and what part of the phase) the user is in. For example, at the end of the eccentric phase of a squat exercise repetition, where the user is at the bottom and should be at the closest to the ground, the application uses sensor readings to determine the value of the cable length at this point. The value of the cable position (an example of a calculated parameter that is used to characterize the path of the actuator) is then compared against a selected threshold (an example of a canonical parameter against which the calculated parameter is compared). The comparison may be performed as part of an evaluation of an expression in a form detection rule. If, based on the cable position, it is determined that the user is below the threshold (and is "low enough") then the user's form is determined to be fine for this portion of the repetition. However, if the user is above the threshold, and is not low enough, this is a signal indicating that the user has bad form for this phase. Detection of the bad form triggers a form feedback event in the system. Feedback is then provided based on the type of the bad form event that is detected. The threshold may be determined in a variety of ways. As one example, the variety is based on a heuristic. In some embodiments, the heuristic is dependent on user height. Other demographic variables (e.g., age, body mass index (BMI)) may also be used to determine appropriate thresholds.

As described above, form detection rules include expressions that are evaluated by comparing calculated parameters (that characterize the path of an actuator) against canonical parameters. The result of the evaluation of the expression indicates whether incorrect form has been detected. In some embodiments, the form detection engine 222 includes a trigger expression language. For example, there is a trigger event for a type of bad form being monitored for. For a type of bad form, there is an expression that defines a set of conditions that, if met, trigger an event (detection of this type of bad form). The conditions are based on an evaluation of variables that correspond, for example, to various sensor readings and measurements.

As will be described in further detail below, various actions may be taken based on triggering of an event. For example, cues are provided to the user based on the type of form event that has been triggered. This includes feedback on form. One example of a cue for form feedback is a voiceover. The type of action to be taken in response to triggering of the form feedback event may be expressed in the rules for the trigger event. Other examples of feedback are provided below.

As shown in the example of the deadlift, the rules for the deadlift include a set of rules for monitoring, during the eccentric phase of a repetition, the cable position relative to a threshold. If the cable position is determined to be above the threshold at the end of the eccentric phase, then it is determined that the user has not gone low enough for this portion of the exercise, which is a type of bad form. As shown in this example, in addition to detecting bad form, the exercise machine determines a specific type of the detected bad form. When the bad form event is triggered, a piece of text may be displayed on the screen (one example of a cue). As another example, a sound may be emitted to notify the user. As another example, haptic feedback such as vibrations is provided to the user through the actuator/handle to let them know of the poor form. As another example, an image or video indicating the bad form and how to correct it is shown. As another example, a video of the user themselves, annotated to point out the bad form, is shown. Multiple types of cues may be provided in combination. In some embodiments, the form feedback cues are calls to action for the user that are specific to the type of bad form (where good form is the absence of such bad form) that was detected. In this example, by identifying a specific type of bad form, the system provides appropriate feedback, such as cueing the user to go lower if they can.

For a single exercise or movement, many different types of bad form may be monitored for. In the example of a deadlift, in addition to determining whether a user has gone low enough at the end of an eccentric phase of a repetition, other types of bad form relevant to the deadlift movement are monitored. As one example, range of motion between repetitions of a set is monitored. If the range of motion decreases by a threshold amount through a set (on either the top and/or bottom of the deadlift movement), this is a sign that bad form has been detected, because loss of range of motion on either side of the movement indicates that the user is not going all the way down. As the system determines what phase of a motion the user is in, the system is able to determine whether the user has not gone up enough or down enough, and then provide appropriate form feedback based on the type of bad form that was detected in which phase of the exercise. For example, if the system determines that range of motion decreased at the top of the deadlift, then the system cues the user to, for example, extend their legs at the top. If the system determines that range of motion decreased on the way down, and the user did not go all the way down, the system provides feedback instructing the user to make sure that they go all the way down. The cues are also provided at an appropriate time (e.g., during the phase of the rep).

As another example, the rules evaluate variables and parameters related to tempo, which are based on the system monitoring sensor readings such as cable velocity and duration of repetition. For example, one type of bad form that is detected with respect to the deadlift exercise is that they are going too fast, particularly on the eccentric phase of the exercise on the way down. In this example, a rule is configured to determine the duration of the eccentric portion of the repetition and compare the calculated duration against a threshold duration. If the duration falls below the threshold (i.e., is too short), then a type of bad form is detected, and the user is cued/given form feedback.

As described above, when a user performs a movement, the application detects what phase of the exercise repetition the user is in. As shown in the above examples, in some embodiments, rules are defined for specific phases of an exercise. For example, certain bad form may depend on different parts of a repetition, where going too fast in the eccentric phase is only applicable to the eccentric part of the repetition.

As another example, suppose that a user is performing a chest fly movement. In a chest fly, examples of bad form or form to be improved are asymmetries, where the right and left arms move different distances. In this case, to determine such bad form, the application monitors the maximum difference between right and left cable lengths throughout the concentric phase, where the maximum difference exceeding a threshold is a signal of a type of bad form being detected. Another example of a type of form that is checked for/monitored at the end of the concentric phase is if the right and left cables are within a threshold of each other (so that they are even at the end of the concentric phase). Thus, as shown here, specific types of incorrect form are monitored for during specific phases of a repetition.

Sensor Fusion

As shown in the examples above, in order to determine the quality of the use of the exercise machine (e.g., to determine the occurrence of incorrect form), the exercise machine is configured to characterize the path of the actuator through space, over time, and determine whether that path is indicative of incorrect form. Characterization of the path includes determining a set of parameters based on sensor readings collected during performance of an exercise movement, where the set of parameters are then compared against a set of canonical parameters to determine the occurrence of bad form. As described above, the exercise machine includes a variety of sensors, located in various portions of the exercise machine (e.g., motor/cable position encoders) and/or external to the exercise machine (e.g., in the IMUs in the actuators). In some embodiments, characterizing the path of the actuator involves fusing or correlating sensor readings from multiple types of sensors.

In some embodiments, sensor data aggregation engine 220 is configured to perform sensor fusion, which includes correlating measurements taken from multiple sensor readings.

As described above, form detection engine 222 is configured to determine form (or the occurrence of instances of bad form) based on various sensor readings and measurements from various sources. The sensor measurements may be used independently or in combination. For example, in addition to detecting form based on cable measurements, form is also monitored based on other types of sensors, such as inertial measurement units (IMUs) and cameras.

Form detection and actuator path characterization are enhanced by performing sensor fusion. For example, while IMUs are beneficial for measuring relative changes, they are less so for determining absolute position. For example, an IMU is able to provide an accurate measurement that the user twisted by a certain short amount within a certain amount of time. However, it would be difficult to use this type of motion sensed by the IMU to determine that the user moved three inches in one direction and a foot in another direction. However, by using cable measurements as a second type of measurement and fusing it with the IMU measurements, the application is able to determine an accurate estimate of absolute position of the actuator. In this way, the actuator path (e.g., how the actuator is moving) is tracked and characterized in 3D space. User form may then be detected by comparing the parameters defining the estimate (characterization) of how the actuator actually moved through space, or via algorithms involving signal processing, machine learning, and/or statistical inference about the likely pattern of motion, against a set of canonical parameters that define the ideal actuator path or threshold deviations from the correct path that indicate or signal bad form.

The following is an example of using sensor fusion. Consider, for example, the bicep curl. One type of bad form that is monitored for is if, during the performance of the exercise, the path of the handle is going side to side. In this example, the application uses the accelerometer of the IMU to determine that there is a change of position. However, if it is determined from the cable measurements (from cable and/or motor position encoders) that there has not been a change in cable length (or below a threshold amount of change in cable length) then the application determines that the handle is moving sideways, and that bad form has been detected. Thus, as shown in this example, accelerometer and cable measurements from different sensors have been fused together to characterize the path of the actuator during performance of the bicep curl.

Measurements from various types of sensors can be combined. For example, in addition to or instead of combining measurements from IMUs with cable measurements, the cable measurements are combined with camera measurements. Any type and number of sensor measurements may be combined together, as appropriate, using the sensor fusion techniques described herein.

As described above, another example of a sensor associated with the exercise machine is a camera. With respect to camera-based sensors, in some embodiments, the exercise machine includes a camera. In some embodiments, the camera provides a field of view that facilitates form detection. In another embodiment, a camera external to the exercise machine is paired with the exercise machine. For example, a smartphone that has a camera is paired with the exercise machine, and form detection is performed by the exercise machine using the information captured by the smartphone. The processing may be performed locally on the exercise machine, on the device that has the camera, or distributed across the exercise machine and the device that has the camera.

The following are example details regarding sensor fusion involving integration of cable measurements, IMU measurements, and camera-based measurements, where such integration allows for more accurate form detection.

As one example, the camera sensor readings may be used to supplement the cable-based or IMU-based measurements. For example, in some embodiments, the cameras are used to determine measurements or estimates with respect to a user's legs. For example, when using the digital strength trainer, the user is holding an actuator with one or more hands, and the legs may be far removed from the actuator(s), making it difficult to deduce or make estimates of what the legs are doing. In this case, a camera or other type of optical sensor may be used to determine where the legs (and joints of the legs, such as the knees or ankles) are. While cable position measurements may indicate how far a user has moved the cable, the cable measurements alone may not be sufficient to indicate whether the user is not extending their arm enough, or whether they have stopped using their legs. In this example, the camera and cable measurements are used together to determine which body part is responsible for a reduced range of motion (which is an example of a type of bad form for certain exercises).

In some embodiments, the measurements from one type of sensor are used as a check or verification on the path characterization determined using information from other sensors. The exercise machine knows what exercise or movement the user is performing or should be performing (e.g., based on what exercise the exercise machine is presenting to the user to perform). Suppose that the user is performing a pulldown movement. Based on the type of exercise to be performed, particular portions of the user's body (e.g., a joint such as their elbow) should approximately be in particular regions or areas. However, if the camera-based position estimate indicates that the elbow is in another region, then the camera-based estimate may be disregarded for that particular joint. With respect to the cable length, if the cable length has been pulled down by a certain amount, then this provides a cable-based estimate of where the joint should be. If the camera-based estimate is not in agreement or consensus, then the camera-based estimate may be disregarded or combined with the cable-based measurements. Similarly, the measurements from other types of sensors such as the IMUs, which are able to provide, for example, a measure of the amount of wrist rotation, may be fused together to provide an improved estimate and improved confidence in the accuracy of the estimated position of different joints for different movements.

Thus, in some embodiments, sensor fusion is used to determine or estimate the position in 3D space (and over time) of different parts of the body. In some embodiments, the measurements from different sensors are fused together using the techniques described above to determine a best estimate of the body (part) position. The best estimate is then used to determine whether the user's form is correct or not.

In some cases, different conclusions (on whether an instance of bad form has occurred) may be reached by different sensors, where the estimates or conclusions do not agree with each other. In some embodiments, performing sensor fusion includes using an algorithm such as a Kalman filter. Here, one measurement or the other is not simply taken. For example, in some cases, the cable measurements in combination with the IMU measurements may be better, while the camera estimates may be better in others. In some embodiments, the filter such as the Kalman filter is used in performing sensor fusion (integration of all sensor information) by taking a weighted average of all three sensor measurements and/or conclusions. For example, suppose that the camera has a certain level of accuracy, and the IMU has a higher level of accuracy. The Kalman filter may perform an average of 90% of the IMU's position estimate and 10% of the camera-based position estimate. On average, this weighted combination results in higher accuracy than using a single measurement. An example of a Kalman filter using camera, IMU, and cable measurements is detecting a user's arm motion during a bench press, which should go close to the torso at the lowest point of the rep. The camera provides an approximate position of the arm accurately, but may be limited by occlusion of the body and clothing. The signal from the IMU signal may be used to increase the accuracy because rotation of the hand is related biomechanically to the elbow moving closer to the body. Lastly, the cable provides more information about the extension of the arm above the body. To find the most accurate estimate of 3D position of joints in the arm, such as the elbow, the most likely positions derived from each sensor are averaged, with more weight given to sensors with more certainty and accuracy. Stated another way, the probability distributions derived from each sensor signal are multiplied and the most likely position is taken from the resulting probability distribution of possible 3D positions. This process is repeated over time, and when the position of the elbow does not come close enough to the torso with high confidence, then form feedback is provided.

The readings and measurements from different types of sensors may come in different forms and at different times. In some embodiments, sensor fusion includes reconciling or correlating the data from multiple types of sensors and performing harmonization.

For example, IMU data may be batched up prior to being sent. In some embodiments, form detection is not performed as sensor readings are made. Rather, the sensor data aggregation engine goes back in time and reviews the batched data to determine form feedback at times in the past.

In some embodiments, performing sensor fusion includes attributing a set of sensor measurements to a given movement performed by a user. As described, determining whether sensor readings are indicative of the occurrence of bad form is dependent on which movement is being performed. That is, while a set of sensor readings may be indicative of bad form for a bicep curl, the same set of sensor readings would not be indicative of bad form for another type of exercise. Thus, in some embodiments, performing sensor fusion includes attributing sensor readings to a movement so that a determination of whether bad form is detected is performed using the appropriate set of collected measurements. For example, movements in a workout may occur back to back. As described above, in some embodiments, the exercise application provides video that shows a virtual coach performing a movement. A portion of text is also presented indicating what a next move will be. In some cases, a user may stop a set early and start the next move because they are impatient, before the video itself has moved to the next movement. Thus, the movement being performed by the user may not be the same as the movement that the video is indicating should be performed. Thus, the sensor measurements recorded for the movement the user is performing do not match with the presented movement. In some embodiments, when determining the appropriate form feedback, the application performs attribution to account for the boundary between movements, where the application determines whether sensor measurements should apply to one movement or another. This is to determine in part, for example, whether what the user is doing corresponds to what portion of a workout is being presented to a user.

In some embodiments, the sensor data aggregation engine includes logic for performing attribution to determine what set of measurements belongs to what movement. In some embodiments, the attribution logic is configured to determine what movement that a user-performed set mostly overlaps. That user-performed set is then attributed to the movement. If a user starts a set during a presented movement, then that user-started set (and the associated set of sensor readings) is attributed to that presented movement. That is, when the user began a set, whatever movement was presented or should be happening is the one to which the set is attributed. In some embodiments, after a set ends, re-evaluation is performed to verify whether the movement was what was expected, as the user could have started a new move at the end of a previous move.

For example, the attribution logic is configured to determine whether they are performing a next move or if they are continuing the previous move again. This may depend on how far into a video clip they are at currently (which corresponds to a movement being presented as part of a routine). In some embodiments, after a user has finished a set, it is determined or re-affirmed what movement the recorded set belongs to. The sensor measurements for the set, when saved, are attributed to the movement decided on by the attribution logic (which may change between the beginning of the set and the re-evaluation at the end of the set).

The following are example factors used to determine attribution. One example factor is whether the user has completed their repetition goal. In some embodiments, the user is determined to have completed their repetition goal if the user has finished most or all of the prescribed repetition for that movement and started another near the end of the video. Thus, the number of repetitions that the user has done is compared against the number of repetitions that is indicated should be done according to the workout routine. In some embodiments, the attribution logic also evaluates how far into a video clip (corresponding to a movement) the user has gone, as well as how far away the end of the video clip is. By using the attribution processing described above, providing erroneous cues (because the incorrect movement was attributed to a form feedback event) is avoided.

Rules

As described above, form processing engine 208 continuously monitors the form of the user when they are performing an exercise by collecting and evaluating various sensor measurements (and fusing it/correlating it, as described above, by performing sensor fusion). In some embodiments, the collected sensor measurements are used to determine a set of parameters that are compared against a set of canonical parameters defined in expressions in rules for detecting form events (e.g., instances of bad form). For example, the rules include expressions that when evaluated, indicate whether a type of bad form with respect to a movement has been detected. In some embodiments, the expression defines a set of operations that compare path characterizing parameters (calculated using sensor measurements taken during performance of the exercise movement) against canonical parameters. In some embodiments, the rules also include the type of actions to be taken (or feedback to be provided) in response to incorrect form being detected. Thus, the rules may be used to detect specific types of bad form, and provide the appropriate corresponding feedback for that type of detected bad form.

The conditions and expressions included in rules that are evaluated to detect incorrect form may be determined in a variety of ways. In some embodiments, expert coaches or trainers that are knowledgeable about what is bad or incorrect form are consulted. Sensor data (e.g., historical sensor data captured from user performance of exercises) is evaluated to determine patterns or signals in the sensor data that correlate or are otherwise indicative of or correspond to bad form. Thresholds (examples of canonical parameters) for determining when bad form occurs or when a rule is to be triggered may be based on heuristics, data analysis, or the output of machine learning models. For example, thresholds may be varied and testing performed to determine when a rule should be triggered and how often. As one example, it is determined how often a change in 10% of the range of motion causes triggering of the rule. A target of 5-10% of sets being triggered may be used to determine what threshold percentage range of motion should be used.

Evaluating Rules

In some embodiments, detecting incorrect form first includes generating a set of parameters based on the sensor measurements that are collected during a workout as the user is using the exercise machine and performing movements. The generated set of parameters will be evaluated against canonical parameters defined for a movement in expressions in rules, where the results of the evaluation will determine whether incorrect form has been detected during performance of the movement.

As described above, sensor measurements are attributed to certain movements. Each type of movement is associated with a set of parameters that are calculated based on sensor measurements attributed to that movement. The parameters associated with the movement are used to characterize the path of an actuator (which is used to determine a characterization of the user's form) when performing that movement. Different types of movements may be associated with different sets of form characterizing parameters.

The parameters determined from the sensor measurements are evaluated against canonical values for those parameters, where the canonical parameters are defined in expressions in the rules. Based on how the determined parameters compare against the canonical parameters, it is determined whether incorrect form (or a deviation from correct form) has occurred. In some embodiments, form detection rules are evaluated using rules evaluation engine 232 of form detection engine 222.

In some embodiments, each movement is associated with a set of rules. Each rule for a given movement is used to determine a certain type of incorrect form with respect to that movement. That is, for a single movement, there may be many types of incorrect forms that may be monitored for. In some embodiments, each movement or exercise is associated with a unique movement identifier (or "movement_id").

In some embodiments, each type of incorrect form to be monitored for is also associated with a unique identifier. In some embodiments, each type of incorrect form to be monitored for is associated with a corresponding expression that is evaluated to determine whether that type of incorrect form has been detected. In some embodiments, the expression defines a set of operations including comparisons between calculated parameters and canonical parameters, where if, as a result of the comparisons, the expression evaluates to true (e.g., where the comparisons result in Boolean values), and is triggered, then the corresponding type of bad form for the movement is detected. In some embodiments, the rule, in addition to including the expression, includes a label indicating the type of bad form that is detected if the expression is triggered. In some embodiments, the label also indicates the type of feedback that is provided in response to the triggering of the expression (and detection of the type of bad form). The expression may be any function of calculated parameters (calculated from sensor measurements taken during performance of an exercise movement by the user) and canonical parameters, as appropriate.

The following is a data structure example of a set of rules used to detect incorrect form when a user performs the ½ kneeling alternating overhead press.

etition count (which repetition the user is on), the prescribed number of repetitions (for this movement), and the phase in which the minimum position was detected. As shown in this example, if the expression evaluates to true (or 1, or any other appropriate value indicating that the trigger condition(s) for the rule have been met), then text-type feedback is provided, where, for example, the text "Lower your arm slower" is displayed on the screen to the user.

As shown in the above examples, the expression includes various combinations of calculated parameters compared with canonical parameters, as well as various operators defining operations involving parameters calculated from sensor measurements and canonical parameters to determine whether the expression is triggered (e.g., evaluates to true/false, 1/0, etc.).

TABLE 2

| id | movement_id | Move | name | expression | type |
|---|---|---|---|---|---|
| zyx | 1234 | ½ Kneeling Alternating Overhead Press | Bring your elbows to your ribs to reset the rep | MinROM > 0.105 && MinROM < 0.5 | Text |
| edf | 1234 | ½ Kneeling Alternating Overhead Press | Lower your arm slower | EccTooFastAllMoves && RepCount < PrescribedReps && PhaseMinPosition > 3 | Text |

Shown in the example of Table 2 are form detection/feedback rules for detecting two types of bad form when a user is performing the ½ Kneeling Alternating Overhead Press. As shown in this example, the movement has a corresponding movement identifier ("movement_id" column). Also shown in this example is that each type of rule/expression for detecting a certain type of incorrect form during the performance of the movement is associated with a corresponding unique identifier ("id" column).

In the first row, which defines a first rule/expression for detecting a first type of bad form is an expression in the "expression" column. The expression defines a set of conditions for determining whether the type of bad form is detected. As shown in this example, the expression includes a set of comparisons of minimum range of motion (to be calculated from measurements taken when a user is performing the exercise) against a set of canonical values of that minimum range of motion parameter. In this example, if the minimum range of motion that is detected (an example of a parameter that is calculated using sensor measurements attributed to when the user is performing that movement) is both greater than 0.105 (an example of a canonical parameter) and less than 0.5 (another example of a canonical parameter), then the expression evaluates to true and is triggered, therefore indicating that the corresponding type of incorrect form has been detected. As shown corresponding to this rule, feedback of type "text" is also provided. In this example, the text cue that is provided (e.g., displayed on a screen associated with the exercise machine) is also the value in the "name" column, which in this example, is "Bring your elbows to your ribs to reset the rep."

The second row of Table 2 corresponds to a second rule for detecting a second type of incorrect form with respect to the ½ Kneeling Alternating Overhead Press movement. As shown in this example, the corresponding expression checks a set of calculated parameters against a set of canonical parameters to determine whether the trigger condition for the expression has been met. In this example, the parameters include whether the eccentric phase was too fast, the rep- The following is an example list of other parameters that are included in expressions usable to detect instances or events in which incorrect form has occurred:

Minimum range of motion

Eccentric Too Fast All Moves

Repetition Count

Prescribed Reps

Phase Minimum Position

Maximum Range of Motion

Minimum Position

Left Right Cable Difference

After Eccentric Phase

After Concentric Phase

Struggling Score

Phase Left Cable Range of Motion

Phase Range of Motion

Phase Left Cable Standard Deviation

Hands Lowering Slowly

Movement is Oscillating

Sudden Jerk Probability

Set Start Position

Phase Right Cable Maximum

Phase Right Cable Minimum

Phase Right Cable Range of Motion

Eccentric Duration

Determining Rules

In some embodiments, rules are generated and/or provided to the client by backend 206. For example, form rules engine 226 of backend 206 is configured to generate form detection rules. In this example, form rules engine 226 includes rules determination engine 228 which is configured to determine form detection rules. In some embodiments, the rules are determined using global user data 218. In this example, generated rules are stored to rules data store 230.

In some embodiments, the parameters for the form event detection rules are based on a combination of domain knowledge (e.g., from experts in biomechanics), as well as a data set including aggregated exercise and user data (e.g., collected and aggregated from exercise machine clients by backend 206 across a population of users). The dataset (e.g., global user data 218) includes, for example, data pertaining to numerous users performing movements or exercises in the same way, following the same coach instructions. In this way, the dataset, is a large, clean, and uniform strength-training dataset. Further, in some embodiments, each user provides demographic information and the exercise machines track their workouts over time, such that the strength-training dataset is also longitudinal, where changes over time may be accounted for. This dataset may be used to train form detection machine learning algorithms to have high accuracy. Further, the machine learning algorithms learn from data in the data set to find or otherwise detect any type of deviation from good form, even if there is no human-provided explicit label for a specific type of bad form.

In some embodiments, machine learning is used to determine the conditions for triggering detection of incorrect form (or deviations from good form). Consider, for example, a bicep curl. One type of incorrect form that often occurs with respect to bicep curls is where the user leans back and tugs hard at the beginning to build a bit of momentum, which allows the user to get past the hardest portion of the exercise, which is at the bottom portion of the repetition. This type of incorrect form is referred to as "jerking." As one example, a model such as a logistic regression is used that checks or otherwise evaluates a set of features that are indicative of such bad form. The model provides as output a probability that the user has conducted that type of incorrect form.

In some embodiments, the model is trained by evaluating historical videos and associated sensor measurements of users performing bicep curls. Each video is labeled either as one in which the user performed jerking at the start of the bicep curl, or one in which jerking did not occur. The labeling may be performed by trainers who are able to identify the type of incorrect form. The model is then trained based on the labeled training data.

In some embodiments, feature engineering is performed to determine the features of the model. The features may be determined based on measurements taken from one or more sensors (e.g., the result of sensor fusion). The following is an example set of features for detecting "jerking" bad form (other features may be included, without limitation): maximum speed within the first 10% of the range of motion of the concentric phase; the ratio of the maximum speed to the average speed; at what percentage of the range of motion in the concentric phase did the maximum speed occur.

As shown in the example above, speed (e.g., based on cable measurements) is determined. The first derivative of motion, velocity, may be considered. Other derivatives of position, such as the second derivative motion, acceleration, may be considered. For example, the third derivative (jerk) and the fourth derivative (snap) may also be considered.

In some embodiments, a type of incorrect form being detected is associated with a corresponding model, where the model for a given type of bad form is used to determine a probability that the bad form has occurred. In some embodiments, the models are used to determine parameters that are used in expressions evaluated to detect bad form.

In some embodiments, the trained models are included in the operating system of the exercise machine (e.g., as an application package).

In some embodiments, when performing an exercise, the probability that a type of behavior has occurred with respect to the exercise is provided as output from the model. This probability is then stored in a variable to be evaluated as a condition in a rule (e.g., used as a calculated parameter as part of actuator path characterization and evaluated in a form detection expression). For example, when a user performs a bicep curl, the probability of bicep jerk is provided as output from a corresponding model and then stored as a variable. This variable is a variable in the expression that is evaluated for detecting bad form. For example, at the end of the phase, relevant features are calculated. The features are then put through the model (which, for example, is hardcoded into the app), where the model then outputs a probability. The probability is then plugged in as a variable from the (string-based) rule (that may come from a remote entity or server). The rule, using the probability as one input (where the probability may be but one parameter that is evaluated against canonical parameters, such as a threshold probability), is then evaluated locally at the client exercise machine to determine whether an instance of bad form of a certain type occurred.

As described above, rules may be written or established to check for certain types of form at various portions (e.g., phases) of a repetition. Rules may also be established to evaluate form at various parts of a set, such as at the beginning of a set, middle of a set, or end of a set. Rules may also be established to evaluate certain types of form on a certain repetition number. As one example, if a user is not positioned correctly near the exercise machine (e.g., the user is standing too close or too far away), then this will impact the angle of the rope and the manner in which force is being applied (e.g., the user may be applying force in the wrong direction). In some embodiments, a rule is established to check early on in a set whether the position of the user is out of bounds. That is, the rule is evaluated and triggered early in a set, within the first several repetitions, so that they may be cued with any form feedback as needed before continuing on incorrectly.

As another example of the type of form feedback that may be provided at different points in a set, correct starting position is monitored for at the beginning of a set. For example, for a bench press, the user should start with their arms locked out. One type of bad form is when a person does not do so, but instead, for example, starts with their arms near their chest. In some embodiments, the exercise machine is configured with a rule which, in the first few repetitions, detects whether the user has started their repetition in the wrong position. Feedback is then provided, for example, to notify the user to start the proper way on the next set.

Thus, as described above, in response to triggering of form detection rules (based on evaluation of expressions that evaluate calculated parameters against canonical parameters), feedback may be provided within a repetition, between repetitions, within a set, between sets, etc. As also shown in the examples above, in addition to including expressions that are evaluated to detect bad form of various types, a rule also includes a corresponding action or set of actions to take in response to detection of the form event of that type.

Training guidance and form feedback may also be provided between workouts, which may include recommending workouts, replacing exercises in workouts (e.g., with simpler versions or variants of movements), etc. Further details regarding training guidance and form feedback are provided below.

Providing Form Feedback

After incorrect form has been detected, the exercise machine performs various actions based on the type of incorrect form that has been detected. As one example, the actions include providing form feedback, which may take various forms. For example, when a specific type of bad form is detected, a cue is provided in real-time to tell the user how to correct their form. For example, if the user does not go low enough in a squat or deadlift, text is presented on the screen and a voiceover is played "Get lower, if you can" at the end of their repetition. In some embodiments, the application causes visual annotations to be displayed on top of the virtual coach's body to visually present where the user's form deviates from the coach's. In some embodiments, video of the user is shown with bad form with visual annotations of the bad form.

Form feedback engine 224 is configured to provide form feedback. In some embodiments, the type of form feedback that is provided is based on the types of bad form events that are detected. In some embodiments, the form feedback that is performed is based on the action that is defined in a form event rule that is triggered (in response to evaluation of a corresponding expression in the rule). In other embodiments, form feedback such as training guidance is based on an evaluation of form events that have been detected over time.
Cues One example of feedback is providing of cues to the exercise user. Cueing engine 236 is configured to provide cues to users of the exercise machine in response to detection of form events (instances of bad form). Different cues are provided to the user based on the different types of form feedback events that are detected. In some embodiments, the cues describe the type of problematic form being detected, and also provide instructions on how to address the detected type of problematic behavior. The cues may be provided aurally, visually, textually, haptically, etc. The following are examples of cues. Feedback cues may be provided in various ways, such as showing text on screen, playing an appropriate voiceover, video, sound, haptics, etc. Feedback may be provided in any form (voiceover, video, sound, haptic, etc.) for the particular part of the body/limb that is offending. For example, vibrating of the right handle is performed if bad form is detected on the user's right limb.

In some embodiments, to promote variety, the system is biased to play voiceover and video that the user has not recently heard or seen.

The form feedback may be provided at various times. For example, the form feedback is provided at the end of a phase of a repetition. In this case, evaluation of form is performed and immediate feedback is provided. As one example of timing, a phase may be several seconds. The feedback may be provided within a second or half of a second of incorrect form having been detected.

The following are examples of providing cues.

As described above, one example of form feedback is providing a voiceover cue. Some movements have what are referred to as "isolation holds." This includes, when performing a repetition, holding the actuator with the arms fixed, but moving with the legs. The legs are performing the reps, and the arms should not be moving. In this example, problematic form is detected if it is determined that the arms are moving when they should not be (e.g., based on cable and IMU-based sensor measurements). For example, the form feedback event is triggered in response to observing changes in cable length, in which case the user is not keeping their arms over their chest as they should be. In this case, in response to detection of the problematic feedback, a cue (e.g., audio cue such as a voiceover) is provided to the user instructing them to keep their hand over their chest.

As another example, suppose that for a movement, the user is supposed to stand up straight and tall, and should not twist their back, which is bad form. In this example, a rule is configured to determine whether the user has twisted their back (e.g., by detecting movement of the cable). In this case, if the rule is triggered and bad form has been detected, a voiceover cue is provided to the user instructing them to stand up straight and tall.

In the case of a bicep curl, when a person has bad form and there is "jerking," oftentimes a user is moving their hips. In some embodiments, in response to detecting jerking during a bicep curl, a cue is provided to the user indicating that they should start the repetition smoothly and keep their hips locked in place.

Figure 3:
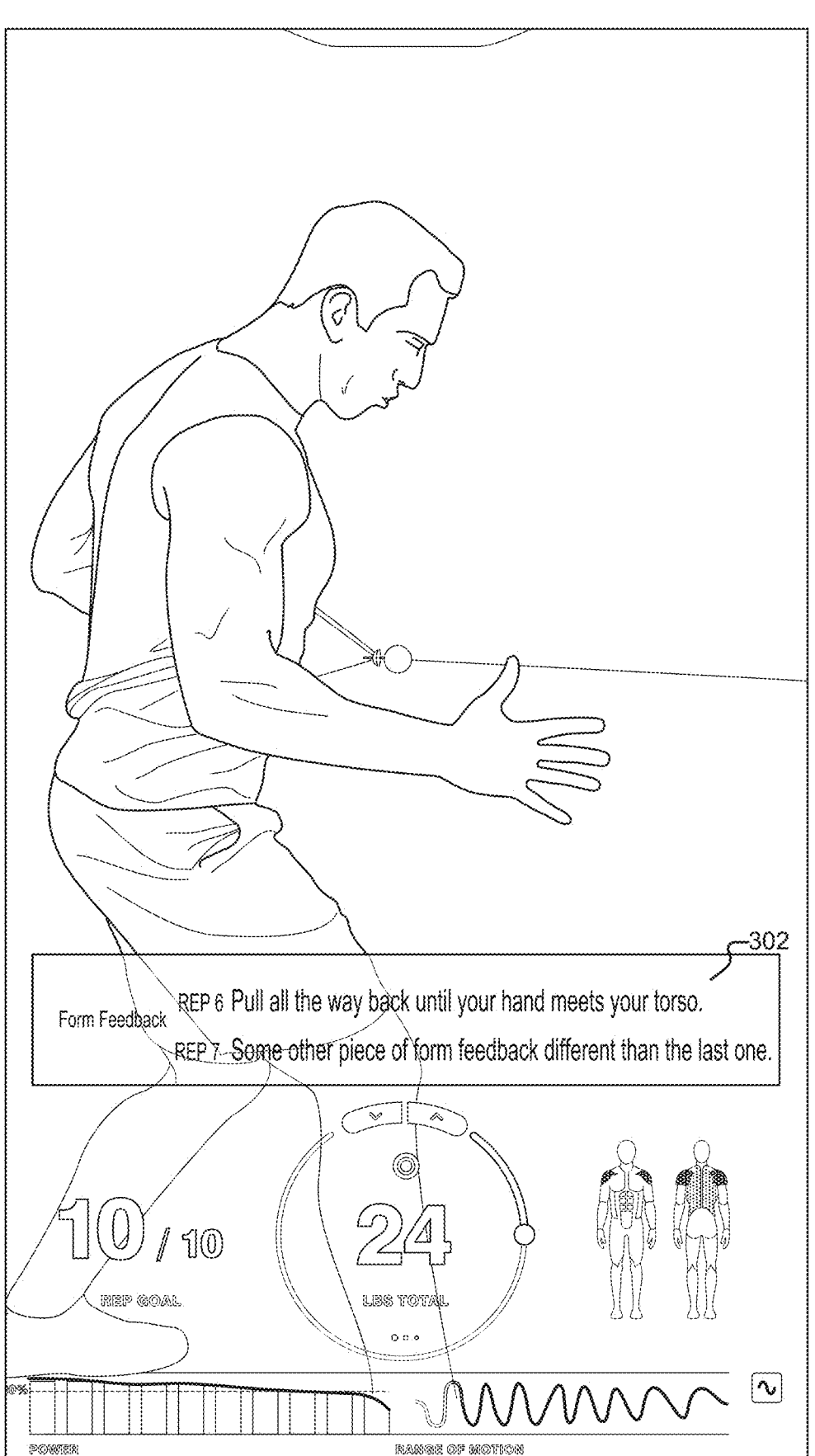
FIG. 3 illustrates an embodiment of providing form feedback.

FIG. 3 illustrates an embodiment of providing form feedback. In this example, text cues (302) are presented on the display of the exercise machine in response to detection of bad form. In this example, one of the pieces of form feedback that is displayed on the screen of the exercise machine is to "Pull all the way back until your hand meets your torso." Other pieces of feedback may also be provided.
Training Guidance Training guidance may also be provided based on evaluation of historical bad form events that have been detected.
Actions Based on Historical Form Events In some embodiments, a record of instances of the occurrence of bad form (also referred to herein as "form events") is kept track of. As one example, when a (bad) form event is triggered, the time at which the form event was detected is recorded. The device (e.g., identifier of the exercise machine) is also recorded. An identifier of the trigger (indicating the type of incorrect form that was detected) is also recorded. Using such information, the set in which the event was detected, as well as the movement that was being performed, may be determined (e.g., based on the attribution processing described above). The rule that was violated is also recorded. The feedback that was provided and when that feedback was provided are also recorded. What repetition and phase of the repetition that the event was detected are also recorded and/or determined from recorded information.

As one example of a data structure for recording such detected form events, a table is implemented that includes columns for the above various fields such as what trigger occurred, on which rep the event triggered, for which movement was the event triggered, from which user, the phase of the rep on which the event was triggered, etc.

Actions may then be taken based on history of recorded feedback events. As one example, when viewing a user's historical data, it is determined (e.g., by the exercise machine and/or the cloud) whether the amount of instances of incorrect form observed for a given user for a particular type of movement is significantly more (e.g., some number of standard deviations more) than an average user. For example, aggregation is performed on the historical information of the user to determine (e.g., by adding up all the times that form events were triggered) the average number of form feedback events the user received for a given move, per set, versus the average number of form events for the particular move across a larger user base (e.g., determined from global user data in global user data store 218). The average number of events for the user is compared with the average number of form events for an average user (determined based on overall user base). If the average number of events for the given user is higher, or above some threshold, various actions may be taken. For example, training guidance is provided. As one example, the user is provided a tutorial on how to perform the move correctly. As another example, for future workouts, the movement that the user has been performing poorly is automatically replaced with a simpler variant of the movement (or one that is easier for a user to have better form). As another example, an exercise that does not use the exercise machine is recommended. In some embodiments, the type of action or feedback provided is based on the type of form feedback event detected. For example, specific videos targeted to a type of form feedback may be provided. As one example, if a user is moving too fast in an eccentric phase of a repetition, this is typically not an issue of skill. Rather, the user simply needs to be told that they are moving too fast and/or that they should slow down. In this case, a video may be provided that indicates to the user the importance of not going too fast. In this case, the user is not necessarily given a simpler move (because the user is able to do the move properly, but has just been performing the move too quickly). However, if the problem is that the user's position is improper (e.g., that they are not going low enough), then this may be an indication that the user is unable to properly perform the move, and that they should not be performing the move. In some embodiments, in such a case, the user is provided with a simpler/easier move to perform. That is, depending on what detected bad form has been triggered, different types of actions may be performed.

Workout Generation/Modification

In some embodiments, detected incorrect form (or deviations from correct form) is used to determine workouts for users. For example, in some embodiments, a next workout and program are recommended. As described above, when a user's form on a certain move is consistently bad (e.g., based on an evaluation of the historical form events), workouts are recommended that use simpler variations of that move that use the same muscles, videos are recommended that help teach a user how to do the move correctly, etc.

In some embodiments, the detected incorrect form events are fed as input into logic or algorithms to determine options for what workouts/programs the user should do next. In some embodiments, the user is presented such options on the display (e.g., in the home screen of the display), along with the ability to manually browse, filter, and search for any other workout/program they might prefer. In some embodiments, the workout/program logic learns and adjusts the next time a user is presented with choices.

Further, in some embodiments, workouts are automatically programmatically created for a user based on input preferences as well as their historical data (e.g., detected bad form events). In some embodiments, video and audio clips are pulled from a library of media clips and then stitched together to form, for example, a virtual coach-led workout.

In some embodiments, based on detection of form feedback events, workouts are adjusted. In some embodiments, the cloud entity (backend 206) includes a system for creating workouts. This includes stitching together clips of video and audio in an automated manner. The outline or plan for the workout is referred to herein as a "timeline," which indicates what events should happen at what times. In some embodiments, flexibility is built in depending on the user's actions. In some embodiments, workouts generated by the server are downloaded by the client exercise machine (e.g., exercise machine 202), where an application running on the exercise machine is then configured to play the workout.

In some embodiments, based on detection of incorrect form events, the plan or timeline for the workout is modified in real-time. In some embodiments, the modification is performed by the client exercise machine. In other embodiments, a request is sent to backend 206 to modify the timeline, where the modified timeline is returned back to the client. In some embodiments, timeline engine 234 of form feedback engine 224 is configured to generate timelines and/or play workout timelines received from backend 206.

The modifications may be made mid-workout. The modifications that may be made include those described above, such as replacing an exercise with which a user is struggling with a simpler variant.

In some embodiments, modifying the workout or timeline includes providing the user an option to change the workout, as described above. For example, based on detected form events, a user interface (UI) option is presented on the screen. The user taps the button and is able to select a different move. In some embodiments, a set of optional or alternative moves is presented. These include moves that are commonly chosen, use the same muscle groups, are versions of the move being replaced, etc. In some embodiments, the options provided are based on the detected form feedback events.

In some embodiments, after the user has selected a different move, the request is sent to backend 206, where the request indicates that the user wants to swap a move for another one. In response to the request, the backend regenerates the timeline (or at least a portion of it). The modified timeline is then sent back to the client to continue playing.

In some embodiments, rather than modifying a timeline mid-workout, the workout is generated from the outset based on the history of detected form events. For example, moves that appear to be problematic for a user (e.g., based on a history of detected form events with respect to those moves) may be swapped out at the beginning of a workout. In some embodiments, rather than modifying an existing workout, a fresh workout is generated that fits the user's needs from the start. Detected form events may be used as one input in generating the new workout personalized or otherwise customized to the user.

In the above example, a workout is generated for the user. In other embodiments, prebuilt workouts are generated, and an appropriate prebuilt workout is recommended or selected for the user.

As described above, the user's progress is tracked over time (e.g., where a history of detected form events is stored and maintained). A user's progress in form for a move may be evaluated over time. If progress has not been made over time (e.g., form for a movement has not improved), different workouts and programs are determined and provided to the user, as described above.

Muscle Group

In some embodiments, an application for presenting exercise related information on a display associated with the exercise machine is configured to present a virtual body with visible muscle groups. This includes displaying a rendering of a person and highlighting muscle groups that should be activated when performing a movement. In some embodiments, if bad form is detected, a relevant portion of the displayed virtual body is lit up (e.g., indicating where the user should be feeling their muscles being activated).

In some embodiments, augmented reality (AR) functionality is provided. For example, the exercise machine represents the user on-screen and embedded within the content (e.g., displayed workout routine) as if they are working out with the coach in the same room. This allows the user to compare, side-by-side, their form with the virtual coach's form, which then allows the user to correct their form by mimicking the coach. In some embodiments, the user's image on screen is annotated with how they should be moving to make the corrections even more important. In some embodiments, the exercise machine displays a "ghost" image on top of a user's video (or virtual reality (VR) or augmented reality (AR)) feed to indicate which part of the body is contributing to incorrect form.

As one example, an image of the user (e.g., based on a camera image or an avatar) is presented on the display. The avatar is dynamic, and mirrors the movements that the user is performing (so that the user can see themselves performing the exercise). In some embodiments, the rendering of the avatar is based on sensor measurements. In some embodiments, highlighting of relevant portions of the avatar is performed based on detected problematic form.

In some embodiments pose estimation and computer vision are performed to determine 3-Dimensional (3D) locations of a user's joints, which allows reconstruction of any view of the user that is desired. Depth sensing technology and time of flight cameras may be used to determine the locations of the user's joints.

Gamification of Form

In some embodiments, gamification of form is performed. As one example, a user is provided a score for their set. If the user performs their set well, with no negative form detected of any sort, then the user receives a high score. If negative or incorrect form is detected, then points are deducted from the score and the score is lowered.

Such gamification allows a user to attempt to beat their previous scores (which in some embodiments are stored as historical information in a record associated with the user). As another example, if multiple users are working out together in a group workout, then everyone participating in the group workout may be presented with a corresponding form score at the end of the set. By comparing form scores to a user's previous best and/or to other people who are working out at the same time or in the past, users are encouraged to use better form in a more enjoyable way. In some embodiments, users are given scores/points during the workout to incentivize following the right form instead of (or in addition to) focusing entirely on how much weight they lifted, and form progress is tracked over time.

A form score may be provided throughout a set and change over the course of a set based on the user's form. In some embodiments, the score is based on the number of form events triggered or cues a user receives. The lower the number of form events, the higher the score. In some embodiments, rather than only checking whether a user has exceeded a threshold specified in a form detection expression in a rule, it is determined how incorrect the user's form is, how much the user deviated from correct form, and/or how close the user was to having correct form. In this way, scores may vary more, as it is not only based on a binary decision of whether a form event was triggered or not. For example, as described in the case of detecting jerking on a bicep curl, the application determines a probability that jerking occurred. If the probability is low, then a better score for that movement is provided. The higher the probability (and therefore more likelihood that poor form occurred), the worse the score becomes.

While examples involving detection of incorrect form have been described herein for illustrative purposes, the techniques described herein may be variously adapted to accommodate detecting good form (and providing feedback accordingly). For example, users may be monitored to detect optimal performance of a movement or exercise, such as in terms of both form, but also speed of the movement, force applied through the movement, etc., where the user may then be provided feedback indicating, for example, that they are performing the movements well. In some embodiments, in response to detection of the user performing an exercise well, positive feedback is provided to the user. Examples of this type of feedback are celebrator visuals/animations on the screen, increased scores or metrics, an increased level, voice over, and/or celebratory sounds.

As one example, a user's motion (and form and performance) during a squat movement may be evaluated to be correct, safe, and optimal as follows:

The pacing is within acceptable ranges as specified by the coaching, typically fast on the upward motion (concentric phase), and slower on the downward motion (eccentric phase)

The power versus the range of motion follows the ideal relationship closely, with the user peaking near the end of the concentric phase The range of motion shows the user is complete and doesn't vary much between reps The user's feet are still and stable on the floor The user's knees shift forward as their torso moves downward The user's back remains straight (core muscles are engaged)

The user keeps their balance and stays level.

In some embodiments, the conditions for detecting good form, such as in the squat example above, are defined using the rules described herein, where the rules for detecting good form are similarly evaluated by comparing various sensor measurements (obtained and combined using, for example, sensor fusion, as described herein) against canonical parameters.

Figure 4:
FIG. 4 is a flow diagram illustrating an embodiment of a process for detecting quality of use of an exercise machine.
Figure 4:
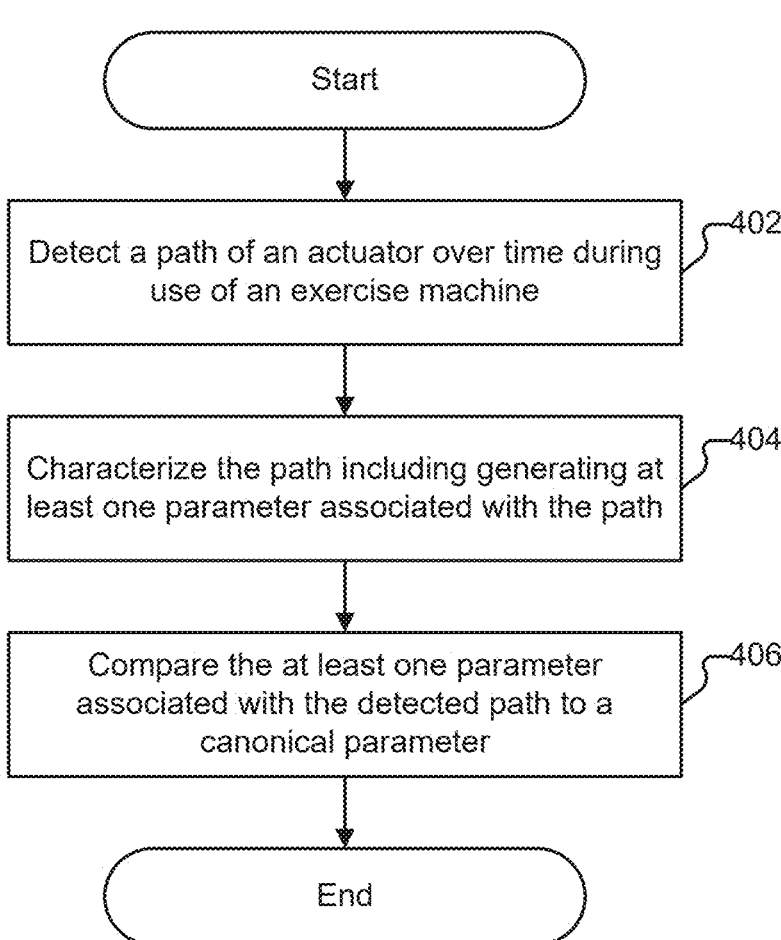

FIG. 4 is a flow diagram illustrating an embodiment of a process for detecting quality of use of an exercise machine, such as a weight training machine. In some embodiments, process 400 is executed by form processing engine 208 of FIG. 2. The process begins at 402, when a path of an actuator is detected over time. As described above, this includes determining, both spatially and temporally, the position of the actuator when the user is performing exercise. The detection of the position/path of the actuator over time is based on measurements from various sensor readings, such as cable position measurements, motor position measurements, IMU measurements, etc.

At 404, the path is characterized. In some embodiments, characterizing the path includes generating a set of parameters associated with the path using sensor measurements. For example, the various sensor measurements are used to determine a set of parameters that are usable to characterize or otherwise determine a form of the user when performing an exercise movement. Examples of such parameters include range of motion of the user, the repetition they are on, the phase of the repetition they are in, the speed at which the user is moving with respect to the phase, cable length differences (e.g., between the two arms), minimum/maximum user positions, the probability of certain types of motions, etc. Further examples of parameters calculated are described above. In some embodiments, characterizing the path includes performing sensor fusion to correlate readings and measurements from multiple types of sensors. Details and examples regarding sensor fusion are described above. In some embodiments, characterizing the path includes attributing a set of sensor measurements to a given movement.

At 406, the generated set of parameters is compared to a set of canonical parameters. For example, the generated set of parameters are evaluated with canonical parameters according to an expression/rule that defines the conditions for which, if met, trigger detection of an event in which incorrect form has been identified. In some embodiments, different expressions are used to identify different types of incorrect form when performing a movement. Multiple types of incorrect form may be monitored for a given type of movement. Examples and details regarding rules and expressions are described above.

Actions may then be taken based on the comparison, such as based on the type of incorrect form that is detected. In some embodiments, the actions that are taken are defined in a rule, where the action is performed in response to an expression in the rule being triggered. In some embodiments, actions are performed using step 504 of process 500. Examples of actions include providing feedback on form and training guidance, such as generating customized workouts based on detected bad form.

Figure 5:
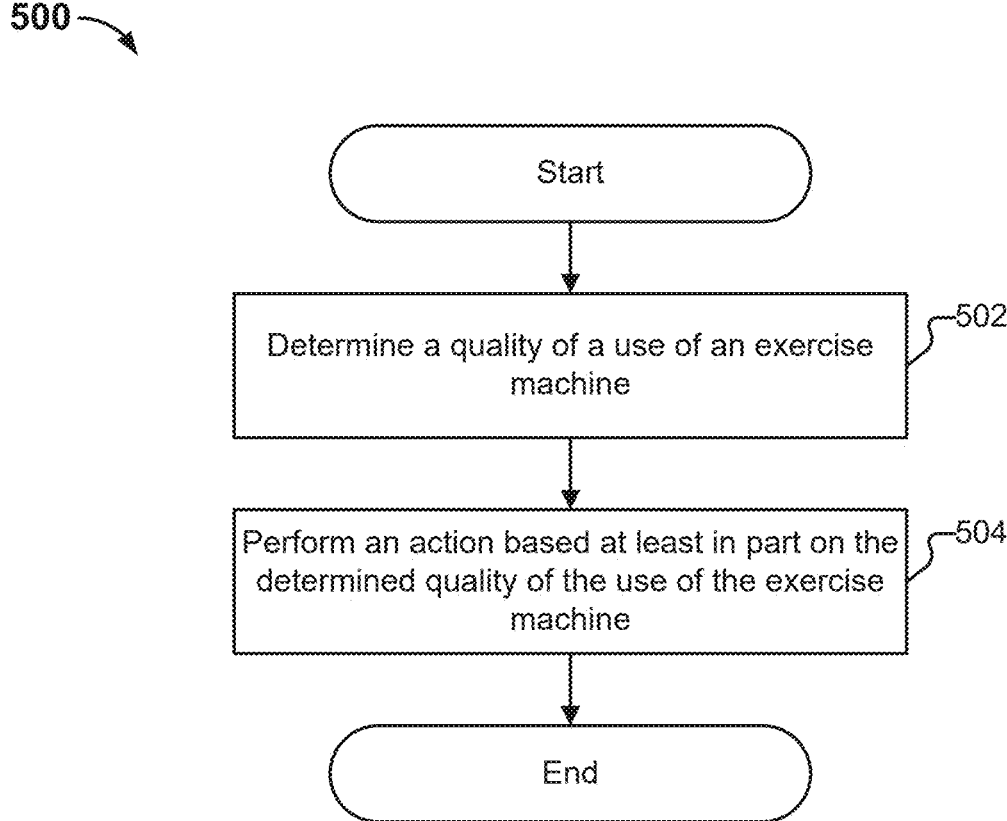
FIG. 5 is a flow diagram illustrating an embodiment of a process for providing feedback on quality of use of an exercise machine.

FIG. 5 is a flow diagram illustrating an embodiment of a process for providing feedback on quality of use of an exercise machine. In some embodiments, process 500 is executed by form processing engine 208 of FIG. 2. The process begins at 502 when the quality of use of an exercise machine (e.g., a weight training machine) is determined. The quality of the use of the exercise machine is determined based on a detected path of an actuator over time. In some embodiments, step 502 is implemented using process 400 of FIG. 4.

At 504, an action is performed based on the determined quality of use of the exercise machine. Examples of actions include providing feedback (e.g., audio feedback, visual feedback, audiovisual feedback, text feedback, haptic feedback, etc.). As another example, workouts are generated or modified based on the determined quality of the use of the exercise machine (e.g., the type of incorrect form that is detected). Examples and details regarding actions (e.g., providing feedback, providing training guidance, etc.) performed in response to detection of incorrect form are described above.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:

one or more processors configured to:

detect a spatio-temporal path of a handle during performance of an exercise movement involving use of a weight training machine;

characterize the spatio-temporal path of the handle including generating at least one parameter associated with the spatio-temporal path of the handle, wherein the spatio-temporal path of the handle is characterized at least in part by fusing together:

(1) at least one of acceleration measurements or rate of rotation measurements from a first sensor comprising an inertial measurement unit embedded within the handle; and (2) cable length measurements from a second sensor different from the first sensor, wherein the cable length measurements from the second sensor are with respect to a cable coupled to the handle;

detect a sub-portion of a repetition of the exercise movement, wherein the sub-portion includes a first phase or a second phase; and compare, based on the detected sub-portion, the at least one parameter associated with the detected spatio-temporal path of the handle to a canonical parameter, the canonical parameter comprising a threshold defined in a form detection expression corresponding to the exercise movement, wherein the at least one parameter includes a first parameter, a second parameter, or both, and wherein the comparing of the at least one parameter associated with the detected spatio-temporal path of the handle to the canonical parameter comprises to:

determine whether the detected sub-portion corresponds to the first phase or the second phase;

in response to a determination that the detected sub-portion corresponds to the first phase, compare the first parameter to the canonical parameter; and in response to a determination that the detected sub-portion corresponds to the second phase, compare the second parameter to the canonical parameter; and a memory coupled to the one or more processors and configured to provide the one or more processors with instructions.

2. The system of claim 1 wherein the one or more processors are configured to compare the detected spatio-temporal path with a previous path.

3. The system of claim 1 wherein the one or more processors are configured to provide feedback based at least in part on the comparing of the at least one parameter associated with the detected spatio-temporal path to the canonical parameter.

4. The system of claim 1 wherein the one or more processors are configured to determine a workout based at least in part on the comparing of the at least one parameter associated with the detected spatio-temporal path to the canonical parameter.

5. A method, comprising:

detecting a spatio-temporal path of a handle during performance of an exercise movement involving use of a weight training machine;

characterizing the spatio-temporal path of the handle including generating at least one parameter associated with the spatio-temporal path of the handle, wherein the spatio-temporal path of the handle is characterized at least in part by fusing together:

(1) at least one of acceleration measurements or rate of rotation measurements from a first sensor comprising an inertial measurement unit embedded within the handle; and (2) cable length measurements from a second sensor different from the first sensor, wherein the cable length measurements from the second sensor are with respect to a cable coupled to the handle;

detecting a sub-portion of a repetition of the exercise movement, wherein the sub-portion includes a first phase or a second phase; and comparing, based on the detected sub-portion, the at least one parameter associated with the detected spatio-temporal path of the handle to a canonical parameter, the canonical parameter comprising a threshold defined in a form detection expression corresponding to the exercise movement, wherein the at least one parameter includes a first parameter, a second parameter, or both, and wherein the comparing of the at least one parameter associated with the detected spatio-temporal path of the handle to the canonical parameter comprises:

determining whether the detected sub-portion corresponds to the first phase or the second phase;

in response to a determination that the detected sub-portion corresponds to the first phase, comparing the first parameter to the canonical parameter; and in response to a determination that the detected sub-portion corresponds to the second phase, comparing the second parameter to the canonical parameter.

6. A system, comprising:

one or more processors configured to:

determine a quality of a use of a weight training machine, wherein:

the quality of the use of the weight training machine is determined based at least in part on a detected spatio-temporal path of a handle when performing an exercise movement;

the quality of the use of the weight training machine is determined at least in part by evaluating a form detection expression corresponding to the exercise movement, wherein the form detection expression comprises at least one threshold;

the evaluating of the form detection expression is based at least in part on fusing together:

(1) at least one of acceleration measurements or rate of rotation measurements from a first sensor comprising an inertial measurement unit embedded within the handle; and (2) cable length measurements from a second sensor different from the first sensor, wherein the cable length measurements from the second sensor are with respect to a cable coupled to the handle; and the evaluating is performed with respect to a detected sub-portion of a repetition of the exercise movement, wherein the sub-portion includes a first phase or a second phase;

the determining of the quality of the use of the weight training machine comprises to:

compare, based on the detected sub-portion, the at least one parameter associated with the detected spatio-temporal path of the handle to a canonical parameter, the canonical parameter comprising a threshold defined in a form detection expression corresponding to the exercise movement, wherein the at least one parameter includes a first parameter, a second parameter, or both, and wherein the comparing of the at least one parameter associated with the detected spatio-temporal path of the handle to the canonical parameter comprises to:

determine whether the detected sub-portion corresponds to the first phase or the second phase;

in response to a determination that the detected sub-portion corresponds to the first phase, compare the first parameter to the canonical parameter; and in response to a determination that the detected sub-portion corresponds to the second phase, compare the second parameter to the canonical parameter; and perform an action that is based at least in part on the determined quality of the use of the weight training machine; and a memory coupled to the one or more processors and configured to provide the one or more processors with instructions.

7. The system of claim 6, wherein performing the action comprises providing feedback based at least in part on the determined quality of the use of the weight training machine.

8. The system of claim 7, wherein providing the feedback comprises providing audio feedback including a voiceover.

9. The system of claim 7 wherein providing the feedback comprises providing haptic feedback, including causing the handle to vibrate.

10. The system of claim 9 wherein the weight training machine includes a plurality of handles, and wherein providing the haptic feedback comprises causing a subset of the plurality of handles to vibrate, and wherein the subset of handles is determined based at least in part on the determined quality of the use of the weight training machine.

11. The system of claim 6, wherein performing the action comprises generating a workout routine, wherein the workout routine is generated based at least in part on the determined quality of the use of the weight training machine.

12. The system of claim 11, wherein generating the workout routine comprises selecting one or more exercise movements to include in the workout routine, and wherein the selected one or more exercise movements to include in the workout routine are selected based at least in part on the determined quality of the use of the weight training machine.

13. The system of claim 12, wherein generating the workout routine comprises modifying an existing workout routine at least in part by substituting an existing exercise movement with a selected exercise movement.

14. The system of claim 13, wherein the modifying of the existing workout routine is performed mid-workout.

15. A method, comprising:

determining a quality of a use of a weight training machine, wherein:

the quality of the use of the weight training machine is determined based at least in part on a detected spatio-temporal path of a handle when performing an exercise movement;

the quality of the use of the weight training machine is determined at least in part by evaluating a form detection expression corresponding to the exercise movement, wherein the form detection expression comprises at least one threshold;

the evaluating of the form detection expression is based at least in part on fusing together:

(1) at least one of acceleration measurements or rate of rotation measurements from a first sensor comprising an inertial measurement unit embedded within the handle; and (2) cable length measurements from a second sensor different from the first sensor, wherein the cable length measurements from the second sensor are with respect to a cable coupled to the handle; and the evaluating is performed with respect to a detected sub-portion of a repetition of the exercise movement, wherein the sub-portion includes a first phase or a second phase;

the determining of the quality of the use of the weight training machine comprises:

comparing, based on the detected sub-portion, the at least one parameter associated with the detected spatio-temporal path of the handle to a canonical parameter, the canonical parameter comprising a threshold defined in a form detection expression corresponding to the exercise movement, wherein the at least one parameter includes a first parameter, a second parameter, or both, and the comparing of the at least one parameter associated with the detected spatio-temporal path of the handle to the canonical parameter comprises:

determining whether the detected sub-portion corresponds to the first phase or the second phase;

in response to a determination that the detected sub-portion corresponds to the first phase, comparing the first parameter to the canonical parameter; and in response to a determination that the detected sub-portion corresponds to the second phase, comparing the second parameter to the canonical parameter; and performing an action that is based at least in part on the determined quality of the use of the weight training machine.

\* \* \* \* \*